US012706206B1

(12) United States Patent
Herman et al.

(10) Patent No.: US 12,706,206 B1

(45) Date of Patent: Aug. 11, 2026

(54) DATA PIPELINE FOR MANAGING AND DETERMINING PERSONALIZED DATA

(71) Applicant: Sleep Number Corporation, Minneapolis, MN (US)

(72) Inventors: Carol Lynn Herman, Minneapolis (MN); Stacy Marie Stusynski, Blaine, MN (US); Vikas Talegaoankar, Livermore, CA (US); Kavita Kolli, Austin, TX (US); Deepika Sikri, Los Gatos, CA (US); Kristy Elizabeth Swenby, Blaine, MN (US); Zvi Eisips, San Jose, CA (US)

(73) Assignee: Sleep Number Corporation

( * ) Notice: Subject to any disclaimer, the term of this patent is extended or adjusted under 35 U.S.C. 154(b) by 140 days.

(21) Appl. No.: 18/196,658

(22) Filed: May 12, 2023

Related U.S. Application Data

(60) Provisional application No. 63/341,701, filed on May 13, 2022.

(51) Int. Cl.
*G16H 40/20* (2018.01)
*G16H 20/70* (2018.01)

(52) U.S. Cl.
CPC ............. *G16H 40/20* (2018.01); *G16H 20/70* (2018.01)

(58) Field of Classification Search
CPC ............................... G16H 40/20; G16H 20/70
See application file for complete search history.

(56) References Cited

U.S. PATENT DOCUMENTS

| | | | |
|---|---|---|---|
| 4,644,597 | A | 2/1987 | Walker |
| 4,766,628 | A | 8/1988 | Walker |
| 4,788,729 | A | 12/1988 | Walker |
| D300,194 | S | 3/1989 | Walker |
| 4,829,616 | A | 5/1989 | Walker |
| 4,890,344 | A | 1/1990 | Walker |
| 4,897,890 | A | 2/1990 | Walker |
| 4,908,895 | A | 3/1990 | Walker |
| D313,973 | S | 1/1991 | Walker |

(Continued)

OTHER PUBLICATIONS

U.S. Appl. No. 09/471,592, filed Dec. 23, 1999, Shafer.

(Continued)

*Primary Examiner* — Allen S Lin

(74) *Attorney, Agent, or Firm* — Norton Rose Fulbright US LLP

(57) ABSTRACT

Disclosed is a data pipeline for managing data for determining personalized data for many users. The pipeline can include a startup manager microservice that receives user input to begin batch processing user data, receives the user data in near real-time, and runs data definition language (DDL) and data manipulation language (DML) scripts at a data store to prepare the data store to be used by other pipeline microservices. The pipeline can include rule engines that generate personalized data based on the received user data, a metrics aggregation microservice that can receive the user data from the startup manager microservice and aggregate the user data in near real-time, a message repository microservice that can store, in the data store, messages generated by the rule engines using the corresponding message templates, and a synchronization microservice to provide communication between the pipeline and user devices.

19 Claims, 9 Drawing Sheets

(56) References Cited

U.S. PATENT DOCUMENTS

| | | | | |
|---|---|---|---|---|
| 4,991,244 | A | 2/1991 | Walker | |
| 5,144,706 | A | 9/1992 | Walker | |
| 5,170,522 | A | 12/1992 | Walker | |
| D368,475 | S | 4/1996 | Scott | |
| 5,509,154 | A | 4/1996 | Shafer et al. | |
| 5,564,140 | A | 10/1996 | Shoenhair et al. | |
| 5,642,546 | A | 7/1997 | Shoenhair | |
| 5,652,484 | A | 7/1997 | Shafer et al. | |
| 5,765,246 | A | 6/1998 | Shoenhair | |
| 5,903,941 | A | 5/1999 | Shafer et al. | |
| 5,904,172 | A | 5/1999 | Gifft et al. | |
| 6,037,723 | A | 3/2000 | Shafer et al. | |
| 6,108,844 | A | 8/2000 | Kraft et al. | |
| 6,161,231 | A | 12/2000 | Kraft et al. | |
| 6,202,239 | B1 | 3/2001 | Ward et al. | |
| 6,397,419 | B1 | 6/2002 | Mechache | |
| 6,483,264 | B1 | 11/2002 | Shafer et al. | |
| 6,686,711 | B2 | 2/2004 | Rose et al. | |
| 6,708,357 | B2 | 3/2004 | Gaboury et al. | |
| 6,763,541 | B2 | 7/2004 | Mahoney et al. | |
| 6,804,848 | B1 | 10/2004 | Rose | |
| 6,832,397 | B2 | 12/2004 | Gaboury et al. | |
| D502,929 | S | 3/2005 | Copeland et al. | |
| 6,883,191 | B2 | 4/2005 | Gaboury et al. | |
| 7,237,287 | B2 | 7/2007 | Weismiller et al. | |
| 7,389,554 | B1 | 6/2008 | Rose | |
| 7,558,622 | B2 | 7/2009 | Tran | |
| 7,865,988 | B2 | 1/2011 | Koughan et al. | |
| 8,120,471 | B2 | 2/2012 | Collins et al. | |
| 8,336,369 | B2 | 12/2012 | Mahoney | |
| D691,118 | S | 10/2013 | Ingham et al. | |
| D697,874 | S | 1/2014 | Stusynski et al. | |
| D698,338 | S | 1/2014 | Ingham et al. | |
| D701,536 | S | 3/2014 | Shakal et al. | |
| 8,769,747 | B2 | 7/2014 | Mahoney et al. | |
| 8,893,339 | B2 | 11/2014 | Fleury et al. | |
| 8,931,329 | B2 | 1/2015 | Mahoney et al. | |
| 8,966,689 | B2 | 3/2015 | McGuire et al. | |
| 8,973,183 | B1 | 3/2015 | Palashewski et al. | |
| D728,254 | S | 5/2015 | Blazar et al. | |
| D737,250 | S | 8/2015 | Ingham et al. | |
| 9,314,118 | B2 | 4/2016 | Blazar et al. | |
| 9,578,941 | B2 | 2/2017 | MacLachlan et al. | |
| 9,730,524 | B2 | 8/2017 | Chen et al. | |
| 9,737,154 | B2 | 8/2017 | Mahoney et al. | |
| 9,830,424 | B2 | 11/2017 | Dixon et al. | |
| D809,843 | S | 2/2018 | Keeley et al. | |
| D812,393 | S | 3/2018 | Karschnik et al. | |
| 9,924,813 | B1 | 3/2018 | Basten et al. | |
| 10,143,312 | B2 | 12/2018 | Brosnan et al. | |
| D840,732 | S | 2/2019 | Peterson et al. | |
| 10,194,753 | B2 | 2/2019 | Fleury et al. | |
| 10,285,508 | B2 | 5/2019 | Rose et al. | |
| D857,433 | S | 8/2019 | Kiekhoefer et al. | |
| 10,531,745 | B2 | 1/2020 | McGuire et al. | |
| 10,539,170 | B2 | 1/2020 | Peterson et al. | |
| 10,575,654 | B2 | 3/2020 | Shakal | |
| 10,677,232 | B2 | 6/2020 | Shakal et al. | |
| 10,729,253 | B1 | 8/2020 | Gaunt | |
| 10,765,224 | B2 | 9/2020 | Chen et al. | |
| 10,813,470 | B2 | 10/2020 | Mahoney et al. | |
| 10,888,173 | B2 | 1/2021 | Shakal et al. | |
| 10,910,102 | B2 | 2/2021 | Agdeppa et al. | |
| 10,993,546 | B2 | 5/2021 | Shakal et al. | |
| 11,001,447 | B2 | 5/2021 | Shutes et al. | |
| 11,085,479 | B2 | 8/2021 | Griffith et al. | |
| 11,096,502 | B2 | 8/2021 | Rose et al. | |
| D932,808 | S | 10/2021 | Keeley | |
| 11,140,999 | B2 | 10/2021 | Peterson et al. | |
| 11,229,297 | B2 | 1/2022 | Gaunt | |
| 11,484,128 | B2 | 11/2022 | Stusynski et al. | |
| 11,508,469 | B2 * | 11/2022 | Collins, Jr. | G16H 40/63 |
| D982,360 | S | 4/2023 | Negus | |
| 11,696,682 | B2 | 7/2023 | Tran | |
| 2002/0069462 | A1 | 6/2002 | Gaboury et al. | |
| 2005/0204475 | A1 | 9/2005 | Schmitz et al. | |
| 2005/0235417 | A1 | 10/2005 | Koughan et al. | |
| 2008/0052830 | A1 | 3/2008 | Koughan et al. | |
| 2010/0043148 | A1 | 2/2010 | Rose et al. | |
| 2014/0250597 | A1 | 9/2014 | Chen et al. | |
| 2015/0007393 | A1 | 1/2015 | Palashewski | |
| 2015/0182418 | A1 | 7/2015 | Zaiss | |
| 2017/0331940 | A1 * | 11/2017 | Simchowitz | H04M 1/72436 |
| 2018/0125259 | A1 | 5/2018 | Peterson et al. | |
| 2018/0350144 | A1 * | 12/2018 | Rathod | G06Q 20/3224 |
| 2019/0082855 | A1 | 3/2019 | Brosnan et al. | |
| 2020/0187667 | A1 | 6/2020 | Shakal | |
| 2020/0359805 | A1 | 11/2020 | Brosnan et al. | |
| 2020/0375369 | A1 | 12/2020 | Negus et al. | |
| 2020/0400135 | A1 | 12/2020 | Shakal et al. | |
| 2021/0134454 | A1 | 5/2021 | Larson et al. | |
| 2021/0145183 | A1 | 5/2021 | Negus et al. | |
| 2021/0145185 | A1 | 5/2021 | Negus et al. | |
| 2021/0177155 | A1 | 6/2021 | McGuire et al. | |
| 2021/0244196 | A1 | 8/2021 | Hilden et al. | |
| 2021/0251392 | A1 | 8/2021 | Shakal | |
| 2021/0330090 | A1 | 10/2021 | Shakal et al. | |
| 2021/0341006 | A1 | 11/2021 | Griffith et al. | |
| 2022/0016480 | A1 * | 1/2022 | Bissonnette | A63B 24/0062 |
| 2022/0103618 | A1 * | 3/2022 | Pinheiro | H04L 67/60 |
| 2022/0192388 | A1 | 6/2022 | Smith et al. | |
| 2022/0218116 | A1 | 7/2022 | Rose et al. | |
| 2022/0273118 | A1 | 9/2022 | Peterson et al. | |
| 2022/0322840 | A1 | 10/2022 | Gaunt | |
| 2022/0365797 | A1 * | 11/2022 | Dykman | H04L 67/125 |
| 2022/0369827 | A1 | 11/2022 | Rose et al. | |
| 2023/0017015 | A1 | 1/2023 | Karschnik et al. | |
| 2023/0027288 | A1 | 1/2023 | Karschnik | |
| 2023/0031563 | A1 | 2/2023 | Molina et al. | |
| 2023/0057322 | A1 | 2/2023 | Shakal | |
| 2023/0063979 | A1 | 3/2023 | Doffing et al. | |
| 2023/0117225 | A1 * | 4/2023 | Porto Guedes | G06Q 10/0633 705/7.27 |
| 2023/0128215 | A1 | 4/2023 | Karschnik et al. | |
| 2023/0148764 | A1 | 5/2023 | Negus et al. | |
| 2023/0218088 | A1 | 7/2023 | Brosnan et al. | |
| 2023/0245780 | A1 * | 8/2023 | Molony | A61B 5/4842 705/3 |
| 2023/0311005 | A1 * | 10/2023 | Salazar | G06N 20/20 463/42 |
| 2023/0389717 | A1 | 12/2023 | Yang et al. | |
| 2024/0056441 | A1 * | 2/2024 | Badr | H04L 63/102 |
| 2024/0176896 | A1 * | 5/2024 | Sanghvi | H04L 9/0825 |
| 2024/0379239 | A1 * | 11/2024 | Samset | G16H 50/30 |

OTHER PUBLICATIONS

U.S. Appl. No. 14/594,843, filed Jan. 12, 2015, Rose et al.
U.S. Appl. No. 18/221,628, filed Jul. 13, 2023, Karschnik et al.
U.S. Appl. No. 18/222,104, filed Jul. 14, 2023, Shakal et al.
U.S. Appl. No. 18/367,634, filed Sep. 13, 2023, Gaunt.
U.S. Appl. No. 18/377,932, filed Oct. 9, 2023, VerBockel et al.
U.S. Appl. No. 18/382,902, filed Oct. 23, 2023, Doffing et al.
U.S. Appl. No. 18/512,568, filed Nov. 17, 2023, Stusynski et al.
U.S. Appl. No. 29/719,090, filed Dec. 31, 2019, Negus et al.
U.S. Appl. No. 29/821,785, filed Jan. 3, 2022, Negus et al.

* cited by examiner

102
Processing Microservice
Receive User Input to Begin Batch Processing of User Data
502
Receive User Data
504
Run DDL and DML Scripts at Data Store
506
104A-N
Rule Engines
Import Rules
512
Parse the Rules to Identify Message Templates
514
Store the Parsed Rules and Message Templates in Persistent Metadata
516
Receive Aggregated User Data
522
Receive Aggregated Historic Data
524
Determine Whether the Parsed Rules are Satisfied
526
Generate Personalized Data
528
Generate Messages About the Personalized Data
530
108
Metrics Aggregation Microservice
Receive User Data
508
Aggregate the User Data
510
110
Historic Import Microservice
Retrieve Historic Data About the User
518
Aggregate the Historic Data
520
106
Message Repository Microservice
Receive Messages
532
Store the Messages
534
322
App svc
Retrieve the Stored Messages
536
Transmit the Messages to User Device(s)
538
501A-N
User Devices
Receive the Messages
540
Output the Messages
542

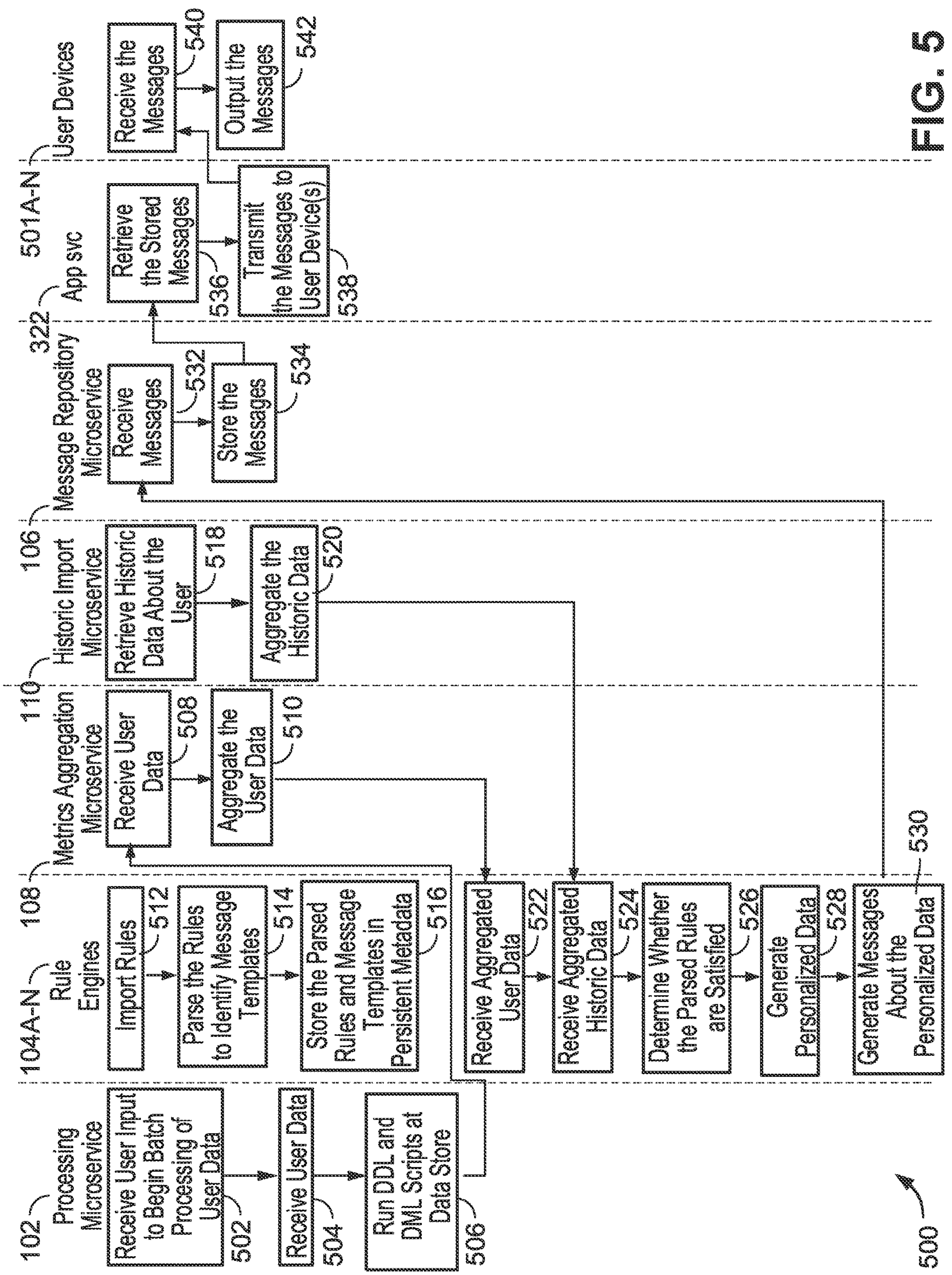

FIG. 5
500

DATA PIPELINE FOR MANAGING AND DETERMINING PERSONALIZED DATA

CROSS-REFERENCE TO RELATED APPLICATIONS

This application claims the benefit of U.S. Provisional Application Ser. No. 63/341,701, filed May 13, 2022. The disclosure of the prior application is considered part of (and is incorporated by reference in) the disclosure of this application.

TECHNICAL FIELD

This document describes devices, systems, and methods generally relating to the management and determination of individually curated content (e.g., personalized data).

BACKGROUND

Users can sign up for different types of services that provide personalized insights to the users based on data associated with the users. For example, a user can sleep in a bed system that includes various sensors that collect information about the user while they are sleeping. The collected information can be provided to a computing system and used to determine personalized insights about the user, such as quality of the user's sleep. Sometimes, the computing system can receive many input signals about the user from many different systems and/or devices, all of which may be used to determine personalized insights about the user.

SUMMARY

The document generally relates to systems and methods for managing large quantities of data and generating personalized data from the large quantities of data. The personalized data can be individually curated content or other personalized insights specific to a user. The disclosed techniques can be used in business flows and insights tools for various types of platforms that offer personalized data to users. More specifically, the disclosed techniques provide a data pipeline that can be used to make data available both quickly and securely such that it can be used by computing systems to generate personalized insights for various users. The data pipeline can provide for making large quantities of data accessible and properly formatted for subsequent use by the computing systems. The data pipeline can include various components for taking in large amounts of data, timely processing the data to generate personalized data, and producing messages about the personalized data that can then be presented in a graphical user interface (GUI) display of a user device of a user associated with the personalized data. For example, various rule engines can be used to generate personalize data. The rule engines can be improved and/or replaced overtime so that the data pipeline can be used for the generation of different types of personalized data.

The backend infrastructure described herein can be used, for example, to aggregate and determine personalized sleep and health insights about sleepers. The determined insights can include suggestions for improving the sleepers' overall sleep and/or health. For example, biometrics data and sleep quality data about a sleeper can be processed through the data pipeline and used to determine accurate insights about the sleeper's sleep and how the sleeper can improve their sleep. The sleeper's data can also be compared with other data that is processed through the data pipeline, such as other sleepers' data, historic sleeper data, data associated with other sleepers who are related to the sleeper, etc., in order to generate accurate and personalized insights for the sleeper. Historic data associated with the sleeper can be initially used to generate personalized data. The historic data may be used again in the future in case of error. For example, historic data can be used to launch data for longitudinal sleep metrics that are already known and used. The historic data can also be used for resolving data issues found in product that may result from systemic issues, such as outages, or coding bugs. Otherwise, newly collected data can be processed through the data pipeline to generate personalized insights for the sleeper.

Although the disclosure is described in reference to sleep insights and health insights, the disclosed techniques can be applied to a variety of other settings in which large quantities of data can be collected and synthesized to generate curated and individualized insights. Although the disclosed techniques can be used for sleep data rolling aggregates, these techniques can also be used in other use cases that involving rolling aggregate metrics.

One or more embodiments described herein can include a data pipeline for managing data for determining personalized data for many users, the data pipeline including: a startup manager microservice that can be configured to: receive user input to begin batch processing of user data, receive the user data in near real-time, and run data definition language (DDL) and data manipulation language (DML) scripts at a data store to prepare the data store to be used by one or more other microservices. The pipeline can also include one or more rule engines that can generate personalized data based at least in part on the received user data, the one or more rule engines being configured to: import, by a rules importer microservice of the rule engine, one or more rules to the data store, the one or more imported rules including message templates for output generated by applying the one or more imported rules to the received user data, parse, by a rules partitioning microservice of the rule engine, the one or more rules to identify the message templates corresponding to each of the one or more rule, and store, by the rules partitioning microservice of the rule engine, the message templates and the parsed rules in persistent metadata. The pipeline can also include a metrics aggregation microservice that can be configured to receive the user data from the startup manager microservice and aggregate the user data in near real-time. The pipeline can include a historic import microservice that can be configured to: retrieve, from a data repository, historic data about a user that is associated with the user data, and aggregate the historic data. The pipeline can also include a message repository microservice that can be configured to store, in the data store, messages generated by the one or more rule engines using the corresponding message templates. The pipeline can also include a synchronization microservice that can be configured to provide communication between the data pipeline and one or more user devices, the messages generated by the one or more rule engines and stored by the message repository microservice being retrieved, by the synchronization microservice, and transmitted to the one or more user devices for presentation in a graphical user interface (GUI) display of the one or more user devices. Each of the one or more rule engines can also be configured to: receive, from the metrics aggregation microservice, the aggregated user data, receive, from the historic import microservice, the aggregated historic data, determine, based on the aggregated user data and the aggregated historic data, whether one or more of the parsed rules are satisfied to generate personalized data for the user associated with the aggregated user data, generate, based on determining whether one or more of the parsed rules are satisfied, messages to be presented at the one or more user devices using one or more of the corresponding message templates, the messages including the generated personalized data, and transmit the generated messages to the message repository microservice for storage.

In some implementations, the embodiments described herein can optionally include one or more of the following features. For example, the rules importer microservice can be configured to import the one or more rules using a Lambda function. The rules importer microservice can be configured to import the one or more rules in a batch upload. Each of the one or more rule engines can include a rule file that indicates (i) a type of personalized data that is determined by the rule engine, (ii) criteria for determining the type of personalized data, and (iii) criteria for a type of output to generate using a corresponding message template. Sometimes, (ii) further can include a time period associated with the personalized data, the time period being at least one of a weekend, a day, a group of days, a week, a month, or a year. The message templates can be used, by the one or more rule engines, to generate the messages in a readable format for users of the one or more user devices. In some implementations, the data pipeline can be a cloud-based service.

In some implementations, at least one of the rule engines can be configured to generate personalized data for the user that indicates monthly or weekly trends based on the aggregated user data and the aggregated historic data. At least one of the rule engines can be a rule-based engine that can be configured to generate monthly health quality scores for the user based on the aggregated user data and the aggregated historic data. At least one of the rule engines can be a rule-based engine that can be configured to generate monthly sleep quality scores for the user based on the aggregated user data and the aggregated historic data. At least one of the rule engines can be artificial intelligence (AI)-based and can be configured to: generate messages about the personalized data for the user, and prioritize, using models, trained with machine learning, and based on the personalized data, sharing of the messages with the one or more user devices. At least one of the rule engines can be a hybrid of a rule-based and AI-based engine that can be configured to generate personalized data about the user based on the aggregated user data and the aggregated historic data.

In some implementations, the one or more rule engines can be executed in parallel. Each of the one or more rule engines can also randomize delivery of the messages to the one or more user devices. The personalized data can include at least one of a sleep score, a quality of sleep score, and a user health score. The user data can include at least one of sleep data, health data, and biometrics data. The user data can be detected by components of a bed system and transmitted to the startup manager microservice by a controller of the bed system. The user data can be received, by the startup manager microservice, in real-time during sleep sessions of the user.

In some implementations, the metrics aggregation microservice can also aggregate the user data on at least one of a weekend, weekday, daily, weekly, monthly, and yearly basis. The message repository microservice can store the generated messages in the data store for a predetermined period of time and archive the generated messages once the predetermined period of time ends. The predetermined period of time can be 3 months from at least one of collection of the user data and determination of the personalized data. One or more of the microservices of the data pipeline can communicate by a simple queue service (SQS) message queue. The personalized data can include one or more suggestions for the user to improve at least one of their sleep and health. The data pipeline further can include a frontend that handles connection between microservices of the data pipeline and the one or more user devices. The frontend can include the metrics aggregation microservice. The data pipeline further can include a backend that handles one or more of the microservices of the data pipeline. The data store can be the same as the data repository. The data store can be different than the data repository. The data pipeline can be instantiated in one or more servers. The data pipeline can be instantiated in one or more virtual machines.

One or more embodiments described herein can include a computerized system for managing data for determining personalized data for many users, the computerized system having: an aggregator that can be configured to: receive aggregation rules and user data from at least one of a data store and user input, retrieve historic data from a historic data store that is related to at least one of (i) a user associated with the user data and (ii) a general population of users having similar attributes as the user, aggregate, based on the aggregation rules, the user data and the historic data, and transmit the aggregated data to at least one rule engine. The computerized system can also have at least one rule engine that can be configured to: receive, from the aggregator, the aggregated data, retrieve, from the data store, rules associated with the at least one rule engine, determine, based on applying the rules to the aggregated data, one or more personalized data for the user, generate, based on the personalized data, messages about the personalized data, and transmit the messages to a messaging service. The computerized system can also include a messaging service that can be configured to: receive, from the at least one rule engine, the messages, store, in the data store, (i) the messages with the user data and (ii) indicators identifying the rules that were applied by the at least one rule engine, and transmit the messages to a report generator. The computerized system can also include a report generator that can: receive, from the messaging service, the messages, generate, based on the messages, at least one report, store, in the data store, the at least one report with the messages, user data, and indicators identifying the applied rules, and transmit the at least one report to a synchronization service. The computerized system can also include a synchronization service that provides communication between the computerized system and at least one user device, the synchronization service being configured to: receive, from the report generator, the at least one report and transmit, to the at least one user device, the at least one report to be outputted in a GUI display of the at least one user device.

In some implementations, the embodiments described herein can optionally include one or more of the following features. For example, the aggregator can also transmit the aggregated data to the synchronization service, and the synchronization service can transmit the aggregated data to the at least one user device to be outputted in the GUI display of the at least one user device. The at least one rule engine can generate the messages using message templates that correspond to (i) the rules that are applied to the aggregated data and (ii) a type of personalized data that is determined by the at least one rule engine. The at least one report can be at least one of a health report, a wellness report, and a sleep report. The at least one rule engine can generate, based on applying the rules to the aggregated data, suggestions for the user to improve their sleep quality. The at least one rule engine can determine personalized data that corresponds to a predetermined period of time, wherein the predetermined period of time is at least one of a weekend, a weekday, a week, a month, and a year.

One or more embodiments described herein can include a data pipeline for managing data to determine personalized data for many users, the data pipeline including: a startup manager microservice that can receive user input, the user input including at least user data, a metrics aggregation microservice that can receive the user data from the startup manager microservice and aggregate the user data, a historic import microservice that can aggregate historic data about a user that is associated with the user data, one or more rule engines that can generate personalized data based at least in part on the aggregated user data and the aggregated historic data, the one or more rule engines each including a rules importer microservice and a rules partitioning microservice, and a message repository microservice that can store, in a data store, messages generated by the one or more rule engines based on the generated personalized data.

In some implementations, the embodiments described herein can optionally include one or more of the following features. For example, the startup manager microservice can also receive the user data in near real-time. The user input can include a request to perform a batch process of the user data, the startup manager microservice being configured to begin batch processing of the user data based on receiving the user input. The startup manager microservice can run data definition language (DDL) and data manipulation language (DML) scripts at the data store to prepare the data store to be used by the one or more other microservices in the data pipeline. The metrics aggregation microservice can aggregate the user data in near real-time.

As another example, the rules importer microservice of each rule engine can import one or more rules to the data store, the one or more imported rules including message templates for output generated by applying the one or more imported rules to the received user data, and the rules partitioning microservice of each rule engine can be configured to: parse the one or more rules to identify the message templates corresponding to each of the one or more rules, and store the message templates and the parsed rules in persistent metadata. As another example, the historic import microservice can be configured to: retrieve, from a data repository, historic data about the user that is associated with the user data, and aggregate the historic data.

Each of the rule engines can generate the messages using corresponding message templates. The data pipeline further can include a synchronization microservice that can provide communication between the data pipeline and one or more user devices. The messages generated by the one or more rule engines and stored by the message repository microservice can be retrieved, by the synchronization microservice, and transmitted to the one or more user devices for presentation in a graphical user interface (GUI) display of the one or more user devices.

In some implementations, each of the one or more rule engines can also: determine, based on the aggregated user data and the aggregated historic data, whether one or more of the parsed rules are satisfied to generate personalized data for the user associated with the aggregated user data, generate, based on determining whether one or more of the parsed rules are satisfied, messages to be presented at the one or more user devices using one or more corresponding message templates, the messages including the generated personalized data, and transmit the generated messages to the message repository microservice for storage. The data pipeline can be instantiated in one or more servers. The data pipeline can also be instantiated in one or more virtual machines.

The devices, system, and techniques described herein may provide one or more of the following advantages. For example, the disclosed techniques can provide for aggregation and formatting of large amounts of data and various types of data from various inputs so that the data can be streamlined and used by computing systems to accurately and efficiently generate personalized data (e.g., individually curated content, personalized insights, etc.).

The disclosed techniques also can provide multiple, streamlined strategies that can be used by computing systems to generate personalized insights for users based on different types of aggregated data, such as sleep and biometrics data. The strategies can be provided by different rule engines and generations (e.g., versions) of the rule engines. The strategies can provide for generation of different types of insights based on different types of data that have been aggregated in the data pipeline. The strategies can also include templates for quickly, efficiently, and accurately generating and formatting notifications (e.g., messages) about the insights for users.

The disclosed techniques can also work on various scales and on longitudinal data. The disclosed techniques can be used to for rolling aggregate metrics and large quantities of data both with efficient use of compute resources and with accuracy. The disclosed techniques can also provide for accurate use and assessment of longitudinal data, can include sleep data or any other type of data metric used in other use cases that can be observed over short or long periods of time. For example, longitudinal data can include time series data. Therefore, the disclosed techniques can provide for efficiently leveraging analysis of different types of data that may otherwise be processed with computationally-taxing, slow, and/or inaccurate processes.

The disclosed techniques can also provide fast and accurate real-time, low latency processing of large quantities of data. Moreover, the disclosed techniques provide for the grouping/aggregating of various different types of data/metrics to generate robust outputs. For example, the disclosed techniques can be used to group time lapse data (e.g., sleep data) with circadian rhythm data and user biometrics in order to generate robust insights into the user's health and sleep quality.

Moreover, the disclosed techniques provide accurate and near real-time or real-time feedback (e.g., health insights) to be provided to users. For example, a user can wake up and within moments of opening/unlocking their mobile device, they can receive health and/or sleep insights based on the sleep session they just had. Thus, sleep and other data about the user can be efficiently and accurately processed in near real-time or real-time using the pipeline described herein to provide the insights that a user typically wants to see about their sleep session once they wake up. Moreover, providing such insights to the user quickly can help the user determine ways they can improve their sleep or health habits before their next sleep session.

The disclosed techniques can also provide quick, accurate, and near real-time or real-time feedback to users in a variety of use cases. For example, the disclosed techniques can be used to provide real-time feedback to users who wear or carry medical devices, such as insulin pumps. A medical device can collect real-time data about a user, which can be processed through the disclosed pipeline to generate quick and accurate outputs to the user. The outputs can include alerting the user when one or more of their levels are off (or declining in real-time) and/or action needs to be taken to ensure the user's health and/or safety. The disclosed techniques can also be used with any other types of biomedical data that can be collected by biomedical devices and/or sensors, including but not limited to blood pressure signals and respiratory signals (e.g., from respiration masks).

As another example, the disclosed techniques can be used to provide real-time feedback based on data collected from solar cells that may impact user safety. The solar cells can include, but are not limited to, temperature and humidity sensors. Any other types of solar cells that collect streaming data can leverage the disclosed pipeline to provide quick and accurate feedback based on the collected data. For example, streams of temperature data can be collected, aggregated, and passed through the disclosed pipeline to determine whether real-time adjustments should be made to a climate in an indoor environment. Streams of temperature data can also be passed through the disclosed pipeline to determine, in real-time, whether an emergency, such as a fire, has started in the indoor environment. As another example, streams of barometric pressure data can be passed through the disclosed pipeline to determine, in real-time and based on dropping pressure values, whether a storm is incoming. As yet another example, streams of carbon monoxide data can be passed through the disclosed pipeline to determine, in real-time and based on rising levels of detected carbon monoxide, whether the indoor environment is unsafe. Similarly, the disclosed pipeline can be used to process streams of data from air quality sensors and other types of sensors that may measure environmental conditions. Such streams of data can be processed through the disclosed pipeline in order to generate accurate, quick, and real-time feedback to users who may be impacted by the developing environmental conditions. Such feedback can be used to protect the users from harm that may develop or is developing from the environmental conditions.

The details of one or more implementations are set forth in the accompanying drawings and the description below. Other features and advantages will be apparent from the description and drawings, and from the claims.

BRIEF DESCRIPTION OF THE DRAWINGS

FIG. 5 is a swimlane diagram of another example process for determining personalized data for a user.

Like reference symbols in the various drawings indicate like elements.

DETAILED DESCRIPTION OF ILLUSTRATIVE EMBODIMENTS

This document generally relates to managing large quantities of data and generating personalized data, such as personalized insights or individually curated content, from such data. The personalized data can be uniquely determined for each user by computing systems that use streamlined data aggregation processes, formatting, and strategies, all of which can be provided by a data pipeline. The data pipeline can be used in various settings and industries that provide curated content for their users. For example, the disclosed techniques can apply to the sleep and healthcare industries. Although the disclosure is described from the perspective of generating insights about sleep quality and health of users, this is merely an example use and the disclosure is not meant to be so limiting. Since more data about a user can be collected and uniformly aggregated using the techniques described herein, computing systems can generate curated and robust insights or other personalized data specific to any user.

Figure 1:
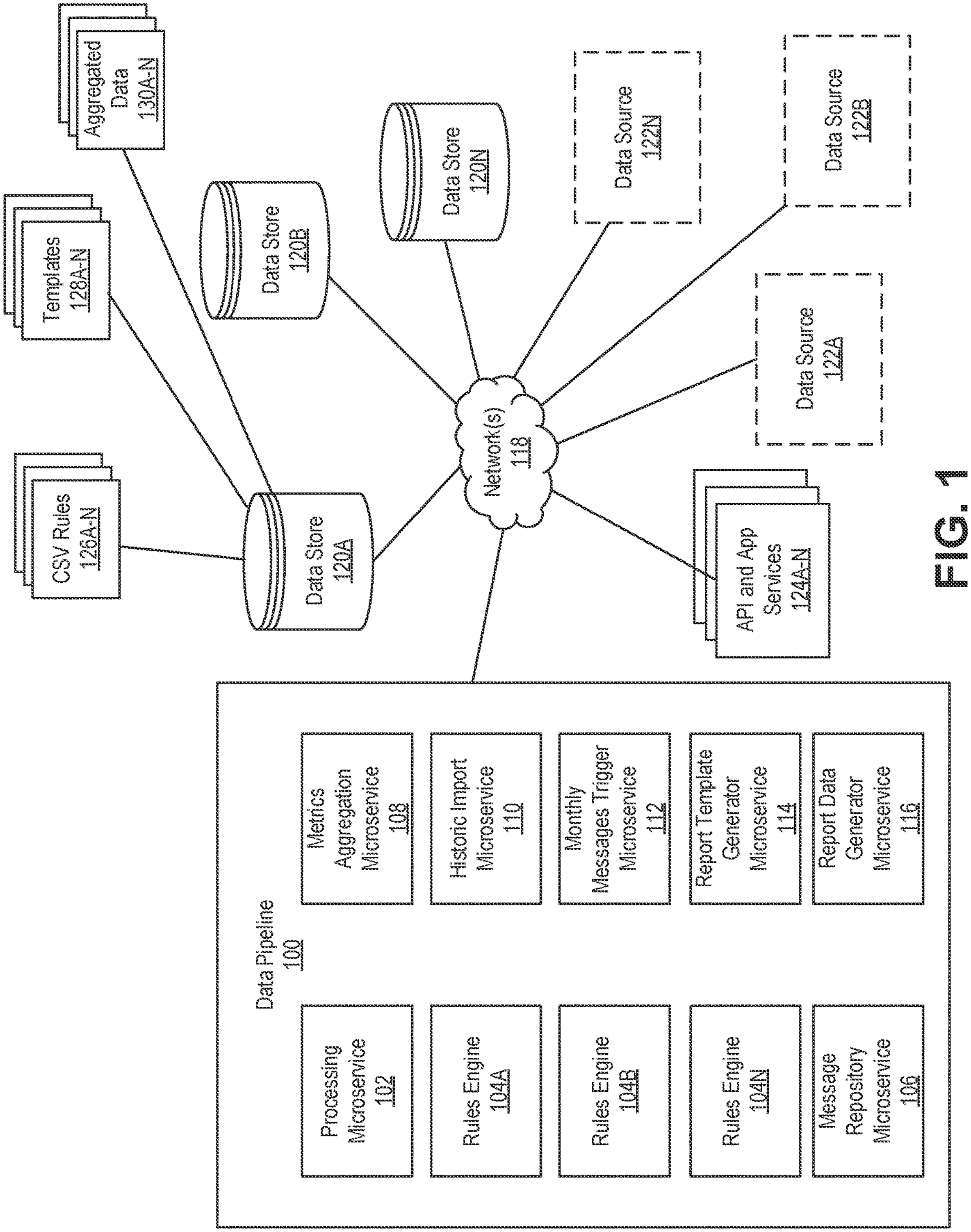
FIG. 1 is a system diagram depicting one or more components that can be used to perform the techniques described herein.
Figure 2A:
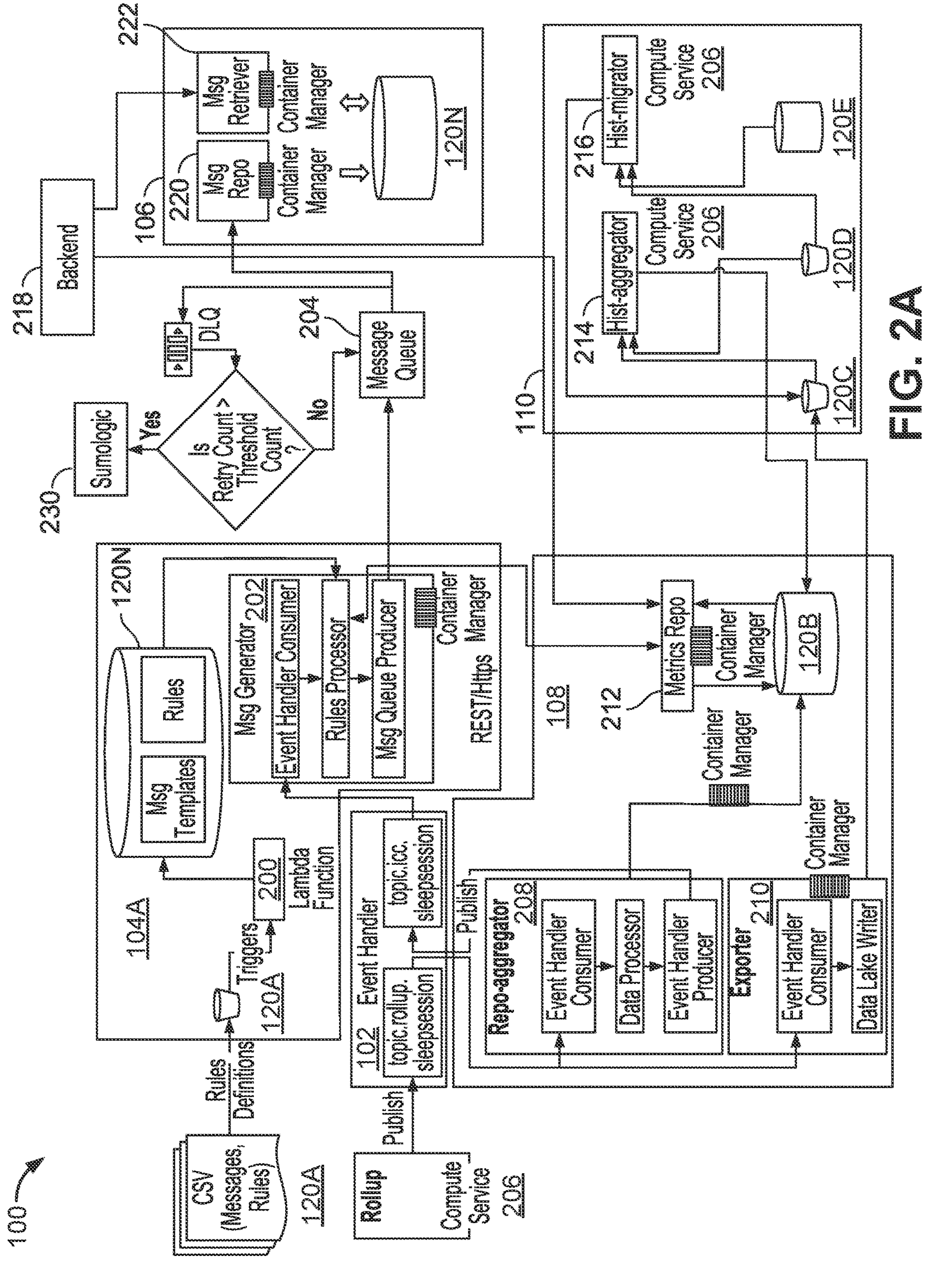
FIG. 2A is an example system architecture having one rule engine that can be used to determine personalized data for many users.
Figure 2B:
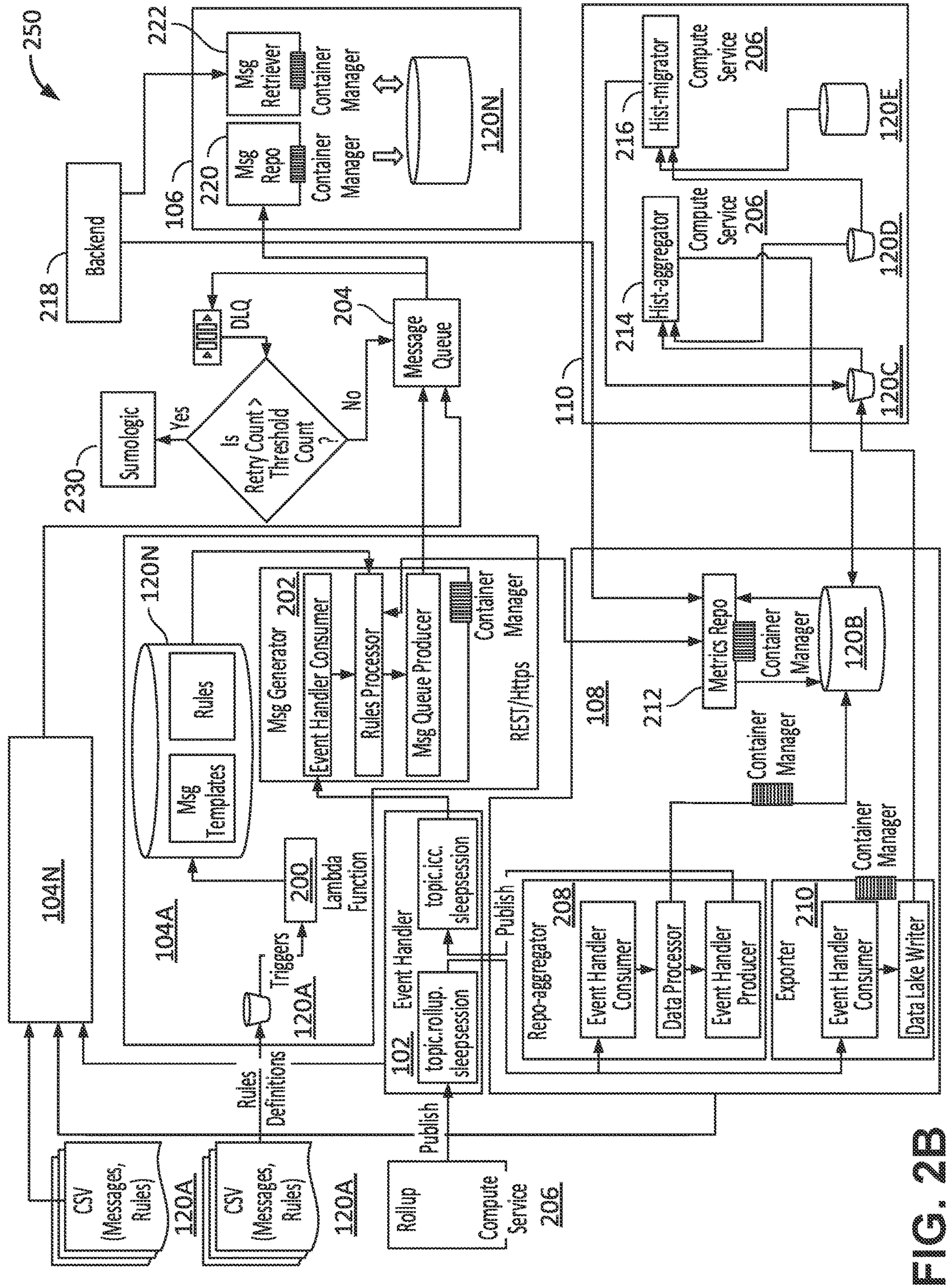
FIG. 2B is an example system architecture having multiple rule engines that can be used to determine personalized data for many users.

Referring to the figures, FIG. 1 is a system diagram depicting one or more components that can be used to perform the techniques described herein. FIG. 2A is an example system architecture having one rule engine that can be used to determine personalized data for many users. FIG. 2B is an example system architecture having multiple rule engines that can be used to determine personalized data for many users. As described herein, any number of rule engines can be executed in a data pipeline. Moreover, the data pipeline can have multiple generations (e.g., versions) of rule engines. Some rule engines can be used for determining trends based on monthly and/or weekly user data. Some rule engines can be more specific and focused on particular types of insights over particular periods of time. Another example rule engine can leverage artificial intelligence (AI) and/or machine learning techniques to generate messages and prioritize delivery of messages to different users. In some implementations, a rule engine can be rule-based, another rule engine can be AI-based, and another rule engine can be a hybrid of both rule-based and AI-based. Sometimes, the rule engines can be executed in parallel. Sometimes, the rule engines can be executed in series. Moreover, in some implementations, selection of the rule engines for execution can be randomized so that the user can receive different messages and different personalized insights during periods of time (e.g., different messages on a daily basis).

Referring to the FIGS. 1 and 2A-B, a data pipeline 100, data stores 120A-N, data sources 122A-N, and API and application services 124A-N can be in communication (e.g., wired and/or wireless) via network(s) 118.

In brief, the data pipeline 100 can be configured to provide streamlined data formatting, aggregation, and processing for generation of personalized data. The data pipeline 100 can be an element of a cloud-based service, a cloud-based computing system, a computing system, and/or a network of computing devices. The data pipeline 100 can be instantiated (e.g., managed, hosted) in one or more services. Sometimes, the data pipeline 100 can be instantiated in one or more virtual machines (VMs). In some cases, in order to accommodate data from globally-distributed sources, elements of the pipeline may be redundantly copied on different hardware systems spread over the geographic area served by the pipeline 100.

The data stores 120A-N can be any type of data storage system, including but not limited to a data repository, a database, a cloud-based data store, and/or a data lake. As an illustrative example, a data lake can be an AMAZON S3-based data lake with APACHE KAFKA. Other data lake implementations are possible. A data lake can be used as a centralized repository for storing structured and unstructured data at any scale. Data may be stored as-is, without having to first structure the data, which allows the data pipeline 100 to quickly and efficiently execute different types of processes, rules, and/or strategies on the stored data. The data stores 120A-N can store various types of information, such as rules that can be applied to different sets of data to generate the personalized data, templates associated with the rules that can be used to generate streamlined messages, notifications, and other reports about the personalized data, data about users (both historic and/or current data) that can be retrieved and used in generating personalized data, and messages that have been generated about personalized insights.

The data sources 122A-N can be configured to provide data, such as unstructured or structured data, to the data pipeline 100 for processing and personalized data generation. The data sources 122A-N can be any type of computing system, network of computing devices, cloud-based service, cloud-based system, and/or user device. The data sources 122A-N may also include applications, software, and other services that can be deployed by various types of computing devices. The data sources 122A-N may optionally communicate with the data pipeline 100 via the network(s) 118. In some implementations, the data sources 122A-N can store data in one or more of the data stores 120A-N, which can then be accessed by the data pipeline 100. As illustrative examples, the data sources 122A-N can include, but are not limited to, a user's mobile device (e.g., smartphone, tablet, smartwatch, other wearable device) that collects (e.g., automatically) health data about the user (e.g., heartrate, respiration rate, temperature, other biometrics data, sleep metrics, etc.), a bed system that collects health and/or sleep data about the user, environmental sensors and/or devices in an environment that collects signals about the user therein, and/or a computing system running an application that allows a user to provide information about themselves or another user to be used in generating personalized insights.

The API and application services 124A-N can provide access to APIs to facilitate communication between components of the data pipeline 100 and other computing systems, such as user devices that host mobile and/or web applications that present the personalized data to respective users. Thus, the services 124A0N can support needs of the mobile and/or web applications so that messages that are generated about the personalized data can be properly conveyed/communicated to the user devices and presented in the mobile and/or web applications.

The data pipeline 100 can include various components that can be used for generating robust personalized data about different users. The data pipeline 100 can include a processing microservice 102, rule engines 104A-N, a message repository microservice 106, a metrics aggregation microservice 108, a historic import microservice 110, a monthly messages trigger microservice 112, a report template generator microservice 114, and a report data generator microservice 116. One or more other, additional, or fewer microservices can be provided and part of the data pipeline 100. Moreover, the data pipeline 100 may include a backend (not depicted) that handles one or more of the components (e.g., microservices, which can be a collection of loosely-coupled services that can be fine-grained with lightweight protocols, subcomponents of a service provided by the data pipeline 100, services comprising the data pipeline 100, etc.) described herein.

The processing microservice 102 can be configured to initiate the processing described throughout this disclosure. The processing microservice 102 can act as a data store manager. For example, as shown in FIG. 5, the processing microservice 102 can receive input from a user or a notification from a computing device that requests for batch processing of user data to begin. The input can include, in some implementations, a file containing user data and/or paths to user data. The file can also include an indication of what type of personalized data is being requested. The processing microservice 102 can collect the user data from the data stores 120A-N and/or receive the user data from the data sources 122A-N (in some implementations, the received input can come from a data source 122A-N, such as a user device). The processing microservice 102 may also determine which rule engines 104A-N to execute based on information in the particular user request.

The processing microservice 102 can therefore be the first microservice to execute in the data pipeline 100. The microservice 102 can receive a rollup function from a compute service 206, as shown in FIGS. 2A-B. The microservice 102 can run Data Definition Language (DDL) and Data Manipulation Language (DML) scripts on the data stores 120A-N. The DDL script(s) can be used to define the data structures (e.g., data stores 120A-N) used by the other microservices in the data pipeline 100. The DML script(s) can be used to manipulate the user data to be used by the other microservices in the data pipeline 100. As a result, the processing microservice 102 can make the data stores 120A-N useable for the other microservices in the data pipeline 100. The processing microservice 102 can also do migration by maintaining a version of the data used by the other microservices in a data store (e.g., any of the data stores 120A-N). The version of the data maintained in the data store can be in KAFKA message format, in some implementations.

The rule engines 104A-N can be executed in the data pipeline 100 to generate one or more personalized data objects based on the user data that is received by the processing microservice 102 in light of rules maintained by the rules engine 104A-N. The rule engines 104A-N can also generate messages for the personalized insights. Each of the rule engines 104A-N can partition rules associated with the engine, determine whether the rule has been met/satisfied, and perform some action in response to that determination. One or more rule engines 104A-N can be selected for execution in the data pipeline 100. For example, as shown in FIG. 2A, only the rule engine 104A is executed in the data pipeline 100. In FIG. 2B, rule engines 104A and 104N are both executed in the data pipeline 100.

As described herein, each rule engine 104A-N can generate a different type of personalized data (e.g., insight) for users. Accordingly, each rule engine 104A-N can include a different set of instructions for execution and generation of personalized data and messages. The instructions for execution can be maintained in a rules file, such as CSV rules 126A-N. The CSV rules 126A-N can apply to comma-separated values (CSV) files, which are text files used by spreadsheets or other data components to organize data into a table. The CSV rules 126A-N can indicate a criteria used (e.g., types of user data, conditions that the user data must satisfy) and a type of personalized data (e.g., insight) that is generated by the particular rule engine 104A-N. Although the criteria used are dynamic and based on the user data, they are templatized such that the same criteria can be applied to generating personalized data for other users. The type of personalized data can based on a variety of categories, including but not limited to weekend trends, daily trends, monthly trends, type of user, etc. The CSV rules 126A-N can also indicate message templates 128A-N to retrieve from one of the data stores 120A-N and use once the personalized data is generated at the particular rule engine 104A-N.

As shown in FIGS. 2A-B, each rule engine 104A-N can have a rules importer 200 and a message generator 202. The rules importer 200, using a Lambda function, can import CSV rules from one of the data stores 120A-N (e.g., the data store 120A) and load the rules into another data store 120A-N (e.g., the data store 120N). The another data store 120A-N can be a data store, such as temporary storage, that is designated for storing data that is currently used in the data pipeline 100 by the rule engines 104A-N to generate the personalized data associated with the user data. Therefore, the rules importer 200 can parse the imported CSV rules and store them in persistent metadata along with message templates.

The message generator 202, as shown in FIGS. 2A-B, can be triggered during a rollup function by a compute service 206 and can generate messages for presentation to users based on the personalized data that is generated by the respective rule engine 104A-N executing its respective pre-defined CSV rule(s) 126A-N. The message generator 202 can, for example, include an event handler consumer, a rules processor, and a message queue producer. The message generator 202 may also include a container manager, which can provide for managing local storage for the generator 202 as the generator 202 generates the messages. In some implementations, the container manager can be a cluster of virtual machines that run various operations/processes for the generator 202 and that can be auto-scaled up or down, depending on needs of the generator 202. The message generator 202 can use the message templates 128A-N, which can be generated for consumption by an end user, like a patient, to generate messages that can be displayed and/or read to the user. The message templates 128A-N, for example, can include rules or conditions that, if satisfied, result in particular messages being generated for the personalized insight. When the rule engines 104A-N generate messages, the messages can be transmitted to the message repository microservice 106. In some illustrative examples, the rule engines 104A-N can communicate with the message repository microservice 106 via KAFKA topics.

The messages can be transmitted to the message repository microservice 106 via a message queue 204, for example. Once in the message queue 204, a determination can be made as to whether a retry count exceeds a threshold count. If the retry count exceeds the threshold count, then the message can be transmitted to sumologic 230. The sumologic 230 can be a logging server, which can be spun up, distributed, and/or centralized. The sumologic 230 can be used for troubleshooting and debugging the data pipeline 100. If the retry count does not exceed the threshold count, the message can remain in the message queue 204. As an illustrative example, a message can persist in the data store 120N in the message repository microservice 106. After a number of attempts (e.g., three to four, five, etc.), the message can be transmitted via the message queue 204 to the sumologic 230 (since the retry count of three to four attempts can exceed the threshold count, which may, for example, be one). For example, soft failures (e.g., database connectivity, request timeout, etc.) can be retried a predetermined amount of times (e.g., 5 times, 3 times, or any other amount of time that is configurable). Retrying a soft failure means that a corresponding request (e.g., message) can go back through the processing pipeline in spite of the failure. After the predetermined amount of times of retrying the request has been exhausted, logging can be performed by the sumologic 230, which can then be consumed by a batch job and/or a manual process to fix data associated with the failure. As mentioned, the sumologic 230 can then process and generate an alert about the message. The alert can notify relevant users (e.g., engineers, developers) to execute an error runbook (e.g., auto heal) to try to fix the data associated with the message. This can be accomplished with an on demand script and/or some manual process, should the aforementioned auto heal fail to fix the data. Each alert can also have a unique failure count and primary identifier of what insight (e.g., health insight, sleep quality insight, etc.) and what user/customer is being impacted by the failure. This type of information can be used for further analysis and debugging of the failure to determine ways by which the data pipeline 100 can be improved so that such a failure is not reoccurring.

The message repository microservice 106 can be configured to store all messages that are generated by the rule engines 104A-N for the personalized data. For example, the microservice 106 can include a message repository 220, as shown in FIGS. 2A-B, that can consume messages that are generated by the rule engines 104A-N from a simple queue service (SQS) and store the messages in one of the data stores 120A-N (e.g., the data store 120N). An illustrative data store can be an AMAZON AURORA database, although other data stores are also possible.

The microservice 106 may also provide access to the APIs and app services 124A-N via a backend 218 so that messages generated by the rule engines 104A-N can be appropriately transmitted, conveyed, and presented to the relevant user devices. For example, the microservice 106 can include a message retriever 222 that can expose representational state transfer (REST) endpoints of the data pipeline 100 to retrieve the messages from the data store. The backend 218 can be used to retrieve the appropriate messages to present to the relevant users at their respective devices. The backend 218 may also provide for generating and presenting graphical user interface (GUI) features for the relevant users that can provide additional information to the users other than just the personalized data messages.

The microservice 106 may store the user data used by the rule engines 104A-N to generate the personalized data. The messages and/or user data can be stored in persistent metadata. The messages and/or user data can be stored in one of the data stores 120A-N for a predetermined period of time. Once the predetermined period of time ends, the microservice 106 can archive the messages and/or user data.

The metrics aggregation microservice 108 can be configured to aggregate the user data as it is received by the processing microservice 102 in real-time (or near real-time). The microservice 108 can include a repository aggregator 208, metrics repository 212, and data store exporter 210, as shown in FIGS. 2A-B. In brief, the repository aggregator 208 can include an event handler consumer, a data processor, and an event handler producer. The aggregator 208 can, based on receiving notification from the processing microservice 102 as a result of the rollup function, calculate the aggregated data for a user and update or create an entry for the user's aggregated data in one of the data stores 120A-N (e.g., the data store 120B in FIGS. 2A-B). The metrics repository 212 can expose a REST API for other services, such as the rule engines 104A-N and/or cloud APIs to obtain aggregated data metrics.

The data store exporter 210 can include an event handler consumer and a data lake writer, and can also be triggered by the rollup function. The exporter 210 can store personalized data to one of the data stores 120A-N (e.g., data store 120C in FIGS. 2A-B), such as a data lake (e.g., AMAZON S3, as an illustrative example). The exporter 210 can, for example, also store messages that are generated for the personalized data as well as correlations that have been made between rules of the rule engines 104A-N and the user data. The exporter 210 can store the personalized data and/or messages for a period of time, such as three months. After the three months have ended, the exporter 210 can archive the personalized data and/or messages. Therefore, the archived data can be used in the data store architecture for troubleshooting, if ever needed. The archived data can also be used for future analytics and AI, such as determining what types of messages can and should be generated by the rule engines 104A-N.

The microservice 108 may aggregate the user data into various categories. For example, for sleep data, the microservice 108 may aggregate the user data into categories of weekend aggregation, week day aggregation, daily aggregation, monthly best sleep score, and/or yearly best sleep score. The categories of aggregation can vary depending on an industry that is using the data pipeline 100. In some implementations, the categories of aggregation can be designated in the user input that is received by the processing microservice 102. The microservice 108 may also aggregate group data. The microservice 108 can aggregate user (e.g., individual) and group data that may be created by various data services (e.g., data sources 122A-N). The microservice 108 can then store aggregated data 130A-N in one of the data stores 120A-N. As an illustrative example, the aggregated data 130A-N can be stored in an AMAZON AURORA database.

The historic import microservice 110 can be configured to collect all other data (e.g., user data and/or group/genus/population data) that can be used to generate various types of personalized data. This personalized data can be historic insights. For example, the personalized data that can be determined, by the rule engines 104A-N, using the collected other data can include, but is not limited to, yearly sleep scores, monthly sleep scores, and/or all-time best sleep scores. The microservice 110 can retrieve the other data from one or more of the data stores 120A-N (e.g., the data stores 120C, 120D, and 120E in FIGS. 2A-B). The microservice 110 can also poll one or more of the data sources 122A-N for the other data, such as compute services 206.

The microservice 110 can include a historic migrator 216 and a historic aggregator 214. The historic migrator 216 can be configured to migrate and verify the other data from one or more of the data stores 120A-N for users of a relevant grouping/category. Migration and verification can occur as a one-time batch process. As an illustrative example, the historic migrator can migrate and verify all sleep session data for all users from an APACHE CASSANDRA data store to an AMAZON S3 bucket data lake. The historic aggregator 214 can be configured to read the migrated data, calculate the aggregated historic data, and store the aggregated historic data in another one of the data stores 120A-N. As an illustrative example, the historic aggregator 214 can read the migrated sleep session data from the AMAZON S3 bucket data lake, calculate the aggregated sleep session data, and store the aggregated sleep session data in the AMAZON AURORA database.

Referring to FIG. 1, the monthly messages trigger microservice 112 can be configured to compile messages to be provided to the user on a monthly basis. For example, the microservice 112 can trigger a process to generate a monthly report. The microservice 112 can run every month (e.g., once a month, at the start of the month, at the end of the month, etc.) and can pick all users (e.g., customers) eligible to receive the monthly reports and add their data into a queue from which to generate their personalized health reports. The microservice 112 can, for example, include a trigger generator and a period trigger generator. Either of the trigger generators can be configured to prepare/compile a list of personalized data messages generation, which can then be sent to the KAFKA topic described herein. Although not shown in FIGS. 1-2, in some implementations, the monthly messages trigger microservice 112 can be part of the message repository microservice 106.

The report template generator microservice 114 can host node.js applications to serve downloading of a wellness report feature at user devices of relevant users. In other words, the microservice 114 can provide templates for presenting a report of data, such as a wellness report, to the relevant user. The microservice 114 can utilize REST endpoint to provide an HTML template for the wellness report (or other reports that can be generated for the personalized data) with a provided JSON report.

The report data generator microservice 116 can make calls to a backend application-svc, the metrics aggregation microservice 108, and/or the message repository microservice 106 to prepare the user data that may be used for building a report, such as the wellness report described in reference to the microservice 114. The report data can be in JSON format. The microservice 116 can save the report data to one of the data stores 120A-N, such as the AMAZON S3 bucket data lake. In other words, the microservice 116 can look at and retrieve historic user data (e.g., sleep data, trends, biometrics, circadian rhythm data points, etc.) in the form of JSON data. Whereas the processing microservice 102 can retrieve real-time user data, the microservice 116 can perform historic data collection (e.g., collecting all user data over a past month, a past two months, a past two weeks, a past six weeks, etc.).

Figure 3:
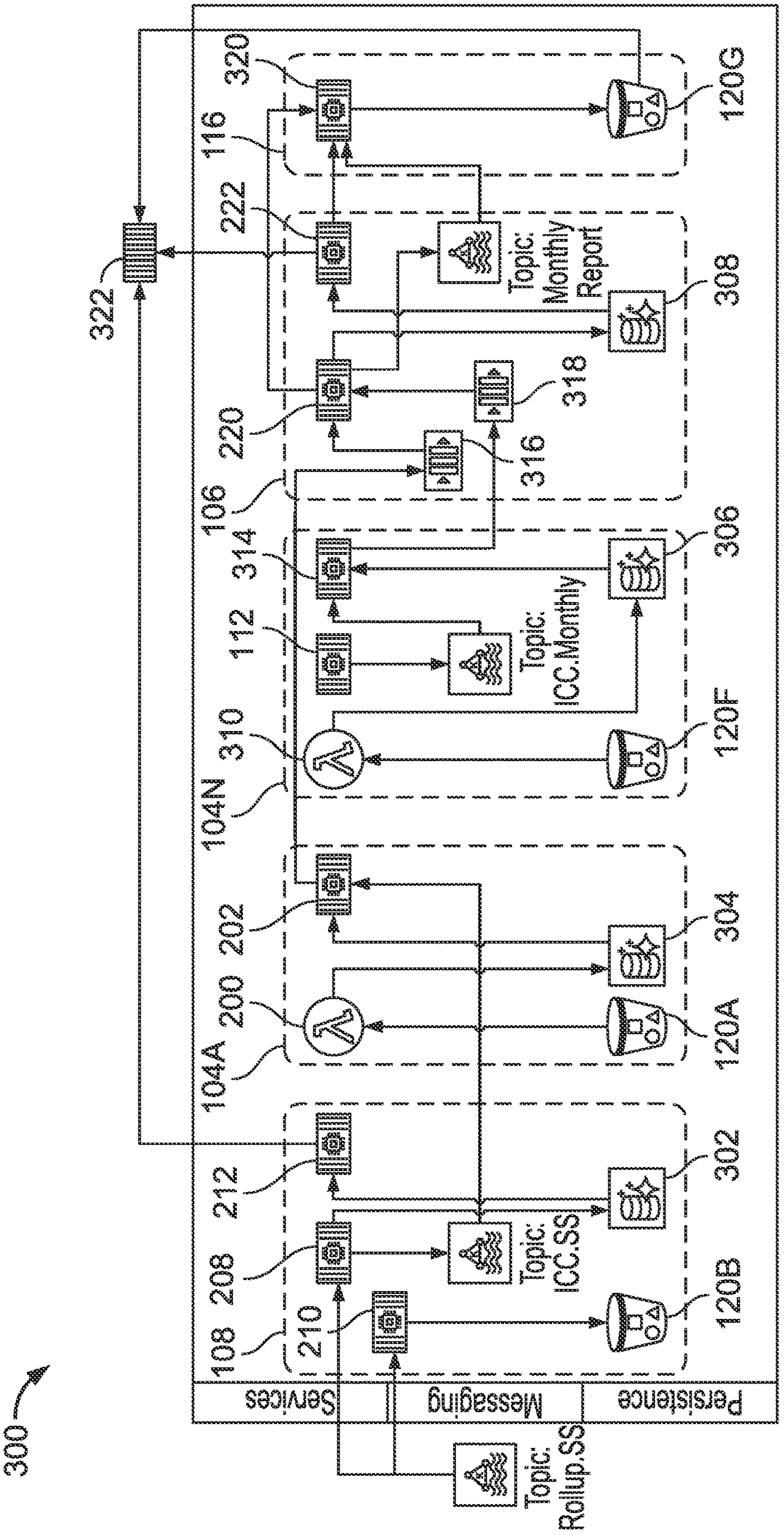
FIG. 3 is an example data flow using the techniques described herein.

FIG. 3 is an example data flow 300 using the techniques described herein. A particular topic can be received with a rollup function by the data store exporter 210 and the repository aggregator 208 of the metrics aggregation microservice 108. As an illustrative example, the topic can be a sleep session topic and can be used to generate a sleep quality score. The rollup function can provide for multiple use cases of the sleep session topic. Data aggregates can be generated by the microservice 108 and stored in the data store 120B. The data aggregates can be generated using corresponding aggregate rules 302. The data aggregates can then be transferred via the metrics repository 212 to the message retriever 222 of the message repository microservice 106. In some implementations, the data aggregates can be transmitted to an application service provider (e.g., application svc) 322, which can cause the data aggregates to be presented to relevant users at their respective user devices. The application svc 322 can provide for synchronization between an application or other software at the user's user device with the data pipeline described herein such that messages generated in the data flow 300 can be presented to the relevant user at their user device.

The message retriever 222 can transmit the data aggregates to the report data generator microservice 116, which can generate a wellness report based on the data aggregate using a generator 320. The wellness report can then be stored in a data store 120G, and transmitted to the application svc 322, which can provide the wellness report for presentation at user device(s) of the relevant user(s).

Still referring to the data flow 300 in FIG. 3 and as described above, the rules importer 200 of the rule engine 104A can use a Lambda function to import rules 302 associated with the engine 104A from the data store 120A. Applying those rules 302 to the user data that was aggregated by the metrics aggregation microservice 108, the rule engine 104A can generate personalized data about a particular user, for which the message generator 202 can generate messages. These messages can be transmitted to the message repository microservice 106.

The rule engine 104N can have a rules importer 310 and a message generator 314. The rule engine 104N may also have a monthly messages trigger microservice 112. The rules importer 310 can use a Lambda function to import rules 306 associated with the engine 104N from data store 120F. Applying the rules 306 to the user data that was aggregated by the metrics aggregation microservice 108, the rule engine 104N can generate personalized data about the particular user, for which the message generator 314 can generate messages. Moreover, the monthly messages trigger microservice 112 can create a list of messages to be generated and presented to the particular user for the month. The message generator 314 can use this list to generate the appropriate messages. In some implementations, as described above, the microservice 112 can include a monthly trigger generator and a periodic trigger generator. The monthly trigger generator can create lists of messages to be generated on a monthly basis while the period trigger generator can create lists of messages to be generated on some predetermined or other periodic basis.

Messages generated by the message generators 202 and 314 can be received at the message repository microservice 106. For example, messages from the message generator 202 of the rule engine 104A can be received in a session SQS queue 316. Messages from the message generator 314 of the rule engine 104A can be received in a periodic SQS queue 318. The messages can be received in different queues because messages from the message generator 202 may be presented to the user regardless of their being a monthly or periodic schedule for presenting messages. Messages from the message generator 314, on the other hand, may only be presented to the user in the order and timing of presentation as determined by the monthly messages trigger microservice 112.

As described above, the message repository 220 of the message repository microservice 106 can consume the messages 308 from the queues 316 and 318. The messages 308 can be consumed at different times. Sometimes, one or more of the messages 308 can be consumed in batch. The message retriever 222 can then retrieve the messages 308 and provide those messages to the application svc 322 to then be presented to the user at the user's device. For example, the message retriever 222 can transmit messages that were maintained in the session SQS queue 316 to the application svc 322. The message retriever 222 can transmit other messages, such as those maintained in the period SQS queue 318, to the report data generator microservice 116. The generator 320 of the microservice 116 can generate a report, such as a wellness report. The wellness report can be a monthly report, as determined by the monthly messages trigger microservice 112, which can define a list of personalized data to include in the monthly report. The report can be stored in data store 120G in association with the particular user, and also provided directly to the application svc 322 for presentation to the user at the user device.

Figure 4:
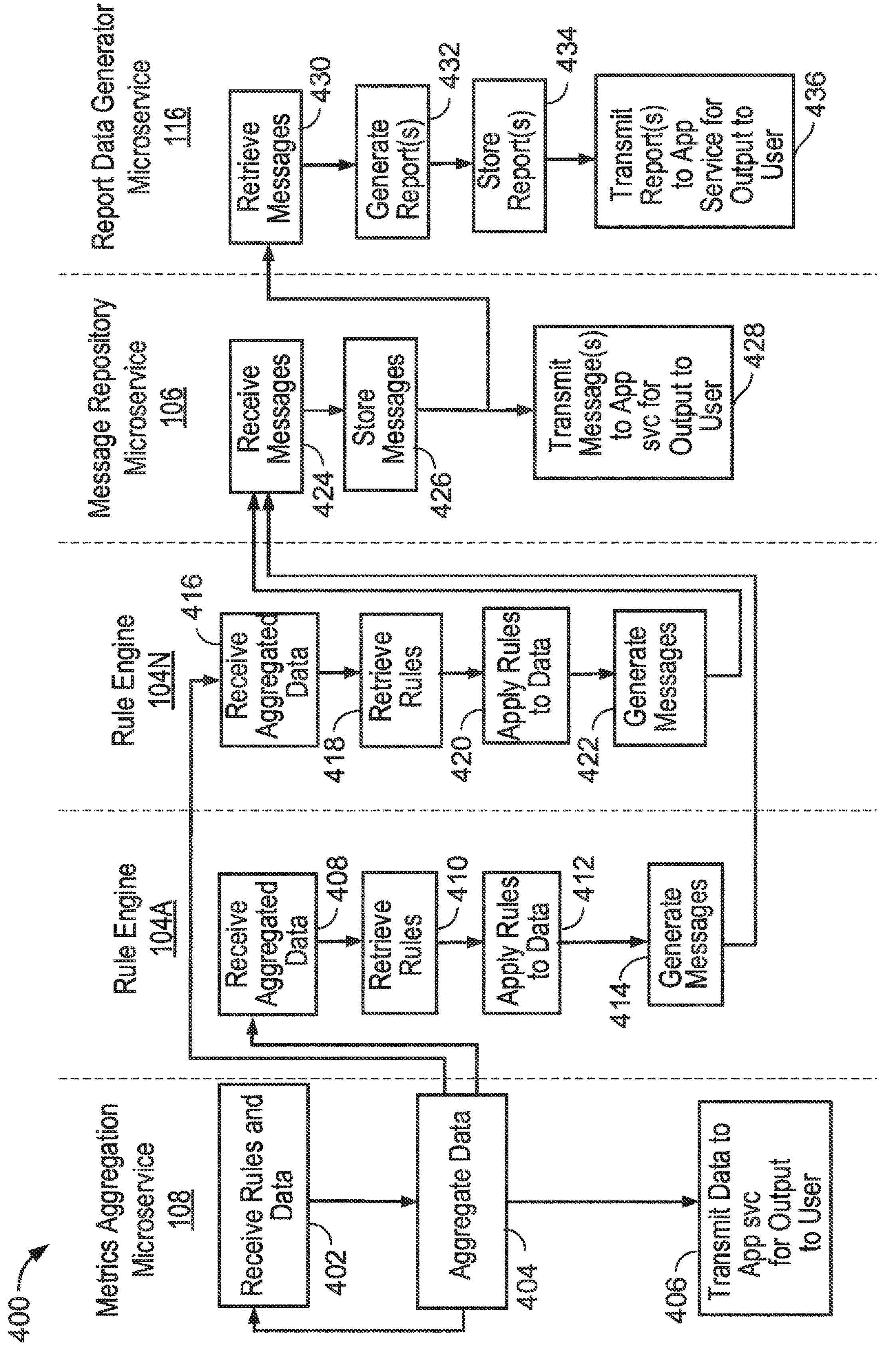
FIG. 4 is a swimlane diagram of an example process for determining personalized data for a user.

FIG. 4 is a swimlane diagram of an example process 400 for determining personalized data for a user. The process 400 can be performed by a combination of components in the data pipeline 100 shown in FIG. 1. For example, blocks can be performed by the metrics aggregation microservice 108, the rule engines 104A-N, the message repository microservice 106, and the report data generator microservice 116. One or more other services, microservices, and/or computing systems can be used to perform the process 400.

Referring to the process 400, the metrics aggregation microservice 108 can receive rules and data in block 402. Block 402 can be performed as part of a rollup function, as described above. In block 402, the microservice 108 can receive aggregation rules from a data store and/or user input. The user data can also be received from the data store and/or user input. The microservice 108 may also retrieve historic data from another data store. The historic data can be related to a user that is associated with the user data and/or a general population of users having similar attributes as the user that is associated with the user data.

The microservice 108 can then aggregate the data in block 404. Using the aggregation rules, the microservice 108 can aggregate the user data and the historic data. The microservice 108 can continue to aggregate the data in block 404 until the microservice 108 no longer receives data in block 402.

The microservice 108 may transmit the aggregated data to the application svc described herein to be outputted for the user at the user's device (block 406). The microservice 108 may also transmit the aggregated data to any of the rule engines 104A-N.

As described herein, the rule engines 104A-N can execute in parallel. Accordingly, each of the rule engines 104A-N can receive the aggregated data (blocks 408 and 416, respectively), retrieve rules associated with each of the rule engines 104A-N (blocks 410 and 418, respectively), apply the rules to the data in blocks 412 and 420, respectively, and generate messages in blocks 414 and 422, respectively. As mentioned, each of the rule engines 104A-N can have its own set of rules depending on use case. The disclosed techniques also provides the advantage of flexibility by allowing one or more of the same rule sets to apply to multiple rule engines 104A-N. The retrieved rules can be used to determine personalized data for the user. As illustrative examples, the personalized data can include suggestions for the user to improve their sleep quality and/or health. At least one of the rule engines 104A-N can be configured to generate personalized data that corresponds to a predetermined period of time, such as a weekend, weekday, week, month, and/or year. Each of the rule engines 104A-N may also transmit the messages to the message repository microservice 106, which can receive the messages in block 424.

The message repository microservice 106 can store the messages in a data store (block 426), as described throughout this disclosure. The microservice 106 may also store indicators identifying the rules that were applied by the rule engines 104A-N in generating the personalize data.

The microservice 106 may transmit some of the messages to the application svc for output to the user in block 428. For example, messages that are generated for a particular session (e.g., a particular night's sleep cycle of the user) can be presented to the user via the application SVC.

The report data generator microservice 116 can retrieve the messages from the data store (block 430), which can be used to generate one or more reports (block 432). In some implementations, the microservice 116 can receive the generated messages from the microservice 106. As illustrative examples, the generated reports can include a health report, a wellness report, and/or a sleep report for the user.

As described in reference to FIG. 3, the rule engine 104N (or any other rule engine executed in the data pipeline) may include a monthly messages trigger microservice 112, which can determine if and when messages are to be included in a monthly or periodic report that is presented to the user. Thus, some of the stored messages may not be transmitted to the application svc in block 428 and instead can be used by the microservice 116 to generate reports of messages.

The generated reports can be stored in a data store in block 434. In some implementations, the microservice 116 may store, in the data store, the generated reports along with the corresponding messages, user data, and indicators identifying the applied rules.

The generated reports can also be transmitted to the application svc for presentation to the user at the user's device (block 436). The report(s) may be transmitted to the application svc at predetermined times, such as at the end of a month when the report(s) is to be presented to the user.

FIG. 5 is a swimlane diagram of another example process 500 for determining personalized data for a user. The process 500 can be performed by a combination of components in the data pipeline 100, shown in FIG. 1, for determining personalized data for many users. For example, blocks can be performed by the processing microservice 102, rules engines 104A-N, metrics aggregation microservice 108, historic import microservice 110, message repository microservice 106, application svc 322, and user devices 501A-N. One or more other services, microservices, and/or computing systems or devices can be used to perform the process 500.

Referring to the process 500, the processing microservice 102, which can be a startup manager microservice, can receive user input to begin batch processing of user data (block 502). The microservice 102 may also receive user data in block 504. The user data can be received in real-time. As merely illustrative examples, the user data can include sleep data, health data, and/or biometrics data. The user data can be received from a variety of different data sources. For example, the user data can be detected by components of a bed system and transmitted to the processing microservice 102 by a controller of the bed system. Sometimes, the user data may be received in real-time during sleep sessions of the user so that insights can be available to the user once they wake up and/or within some period of time from waking up (e.g. 30 seconds, 1 minute 3 minutes, 5 minutes, etc.).

The microservice 102 may also run DDL and DML scripts at a data store in block 506 to prepare the data store to be used by one or more other microservices described herein.

Next, the microservice 102 can transmit the user data to the metrics aggregation microservice 108, which can receive the data in block 508. The microservice 108 can then aggregate the user data in block 510. The microservice 108 may aggregate the user data in near real-time. Moreover, the microservice 108 can aggregate the user data on a weekend, weekday, daily, weekly, monthly, and/or yearly basis. In some implementations, the data pipeline described herein can include a frontend that handles connection between the microservices of the pipeline described herein and the user devices 501A-N. The metrics aggregation microservice 108 can sometimes be included in the frontend.

At the same, similar, or different time as blocks 508-510, the historic import microservice 110 can retrieve historic data about the user (block 518) from one or more data repositories and/or data sources. Such data repositories may or may not be the same as the other data stores described in reference to the process 500. The microservice 110 can retrieve historic data about a user that is associated with the received user data (block 504). The microservice 110 may then aggregate the historic data in block 520. The historic data may also be aggregated in near real-time.

At the same, similar, or different time as blocks 508-510 and/or 518-520, the rule engines 104A-N can import their respective rules in block 512 using a rules importer microservice of the respective rule engine. The rules importer microservice can import the rules using a Lambda function. The rules may also be imported in a batch upload. The imported rules can include message templates for output generated by applying the imported rules to the user data.

The rule engines 104A-N can each parse the rules to identify message templates in block 514 using a rules partitioning microservice of the respective rule engine. The message templates can correspond to each of the rules. The rule engines 104A-N can also store the parsed rule and message templates in persistent metadata in block 516, which can be performed by the rules partitioning microservice.

The rule engines 104A-N, which can generate personalized data based at least in part on the received user data (block 504), can receive the aggregated user data from the metrics aggregation microservice 108 in block 522. The rule engines 104A-N may also receive the aggregated historic data from the historic import microservice 110 in block 524. In some implementations, all of the rule engines 104A-N can receive the same data set of aggregated historic data, however each of the rule engines 104A-N can then filter the data and use specific data to perform their respective processing. In some implementations, one or more of the rule engines 104A-N can receive subsets of the aggregated historic data (e.g., already filtered for the particular processing performed by the respective rule engines 104A-N). In some implementations, the data received by the rules engines 104A-N can be in the form of all-time aggregated data. Additionally, each of the rule engines 104A-N can include a rule file that indicates (i) a type of personalized data that is determined by the rule engine, (ii) criteria for determining the type of personalized data, and (iii) criteria for a type of output to generate using a corresponding message template. The criteria for determining the type of personalized data can also include a time period associated with the personalized data, such as a weekend, a day, a group of days, a week, a month, or a year. The time period can be used by the rule engines 104A-N to determine what aggregated historic data to use in generating the personalized data for the respective user.

In some implementations, the rule file can also indicate what type of data can be used to generate the personalized data. For example, the type of data can include, but is not limited to, biometrics, sleep information, and circadian information. As illustrative examples, the type of personalized data that is determined by the rule engine using the different types of data can include, but is not limited to, general trends about the user's sleep over one or more periods of time, more detailed trends about the user's sleep in one or more periods of time (which can be presented in a report, such as a monthly report), detailed trends about particular categories of personalized data, such as circadian rhythm associated with the user, patterns of consistent or inconsistent sleep, whether the user met one or more sleep goals during one or more periods of time, and other insights.

Using the received data and based on the information included in the rule file, the rule engines 104A-N can each determine whether one or more of their respective parsed rules are satisfied (block 526). The rule engines 104A-N can generate personalized data for the user associated with the aggregated data based on the determination of whether the respective parsed rules are satisfied in block 528.

As described throughout this disclosure, at least one of the rule engines 104A-N can be used to generate personalized data for the user that indicates monthly or weekly trends based on the aggregated user data and the aggregated historic data. As merely illustrative examples, the personalized data can include, but is not limited to, a sleep score, a quality of sleep score, and a user health score. The personalized data may also include, but is not limited to, suggestions for the user to improve their sleep and/or health.

Sometimes, at least one of the rule engines 104A-N can be a rule-based engine that can generate monthly health quality scores for the user based on the aggregated user data and the aggregated historic data. Sometimes, at least one of the rule engines 104A-N may also be a rule-based engine that can generate monthly sleep quality scores for the user based on the aggregated user data and the aggregated historic data. In some implementations, at least one of the rule engines 104A-N can be a hybrid of rule-based and AI-based.

Moreover, the rule engines 104A-N can generate messages about the personalized data using the message templates that were stored in persistent metadata (block 530). The rule engines 104A-N may also determine whether to randomize delivery of the messages to the one or more user devices 501A-N. The message templates can be used to generate the messages in a readable format for the users of the user devices 501A-N. The messages can be presented at the user devices 501A-N using one or more of the corresponding message templates. The messages can include the generated personalized data. In some implementations, at least one of the rule engines 104A-N can be AI-based and can generate messages about the personalized data for the user and prioritize, using machine learning trained models and based on the personalized data, sharing of the messages with the one or more user devices 501A-N.

The aforementioned models can be trained using a training data set including data of users who are signed up to receive personalized data, longitudinal data that has been collected over some period of time (e.g., over a last few years, such as one to five years of collection) for various users, and/or sleep data for various users. The models can be trained using supervised learning. For example, a set of data (e.g., the training data set or a portion thereof) can be provided as input to a model, for which correct outputs are already known. Output generated by the model can then be compared to known relationships between the input and the expected/correct outputs in order to predict future inputs. The models can be trained to have high accuracy. One or more other machine learning techniques can also be leveraged and used to train the models described herein.

The generated messages can be transmitted to, and received by, the message repository microservice 106 (block 532). In some implementations, the microservice 106 may also receive any of the parsed rules, aggregated user data, aggregated historic data, and/or personalized data that was used to generate the messages. Accordingly, the microservice 106 can store the messages in a data store (block 534). The microservice 106 may also store any other data that is received from the rule engines 104A-N. The microservice 106 can store the generated messages in the data store for a predetermined period of time, then archive the generated messages once the predetermined period of time ends. The predetermined period of time can be, for example, three months from collection of the user data (block 504) and/or determination of the personalized data (blocks 526-528).

The application svc 322 can retrieve any of the stored messages at one or more times (block 536). For example the application svc 322 can retrieve the stored message(s) for daily insight generation and requests. The application svc 322 can also retrieve the stored message(s) on a monthly basis for health or other insight reports that are generated and requested on a monthly trend. In some implementations, the stored message(s) can be retrieved at other times, such as every two weeks, every 3 weeks, every six weeks, every two months, etc. The application svc 322 can then transmit the retrieved message(s) to the user devices 501A-N (block 538). As described herein, the application svc 322 can be a synchronization microservice that can provide communication between the data pipeline and one or more user devices 501A-N.

Accordingly, the user devices 501A-N can receive the message(s) in block 540 and output the message(s) for presentation in a graphical user interface (GUI) display of the user devices 501A-N (block 542).

Figure 6:
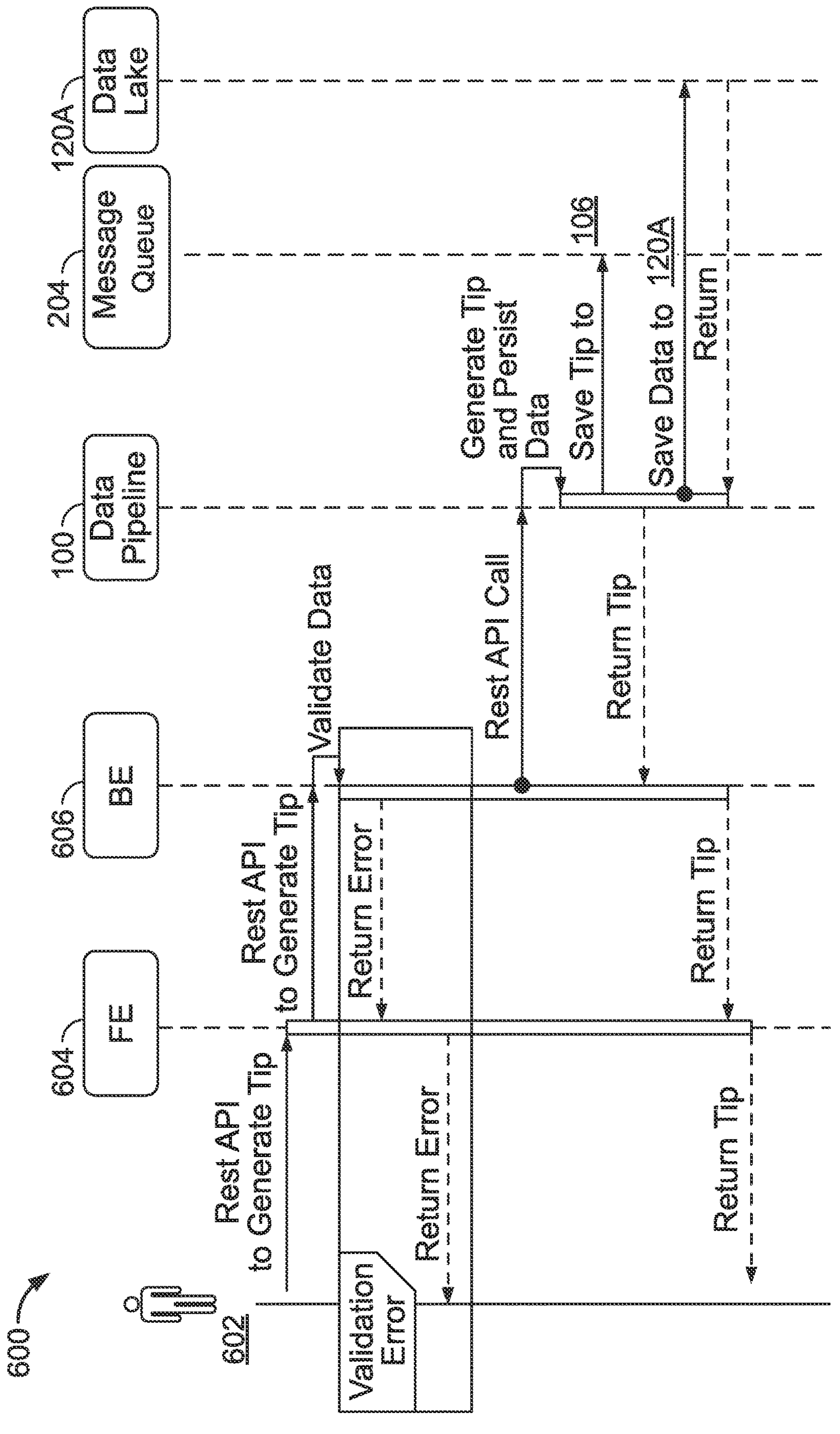
FIG. 6 is a swimlane diagram of a process for generating a tip based on the personalized data that is determined for the user.

FIG. 6 is a swimlane diagram of a process 600 for generating a tip (e.g., a type of personalized data) based on the personalized data that is determined for the user. The tip can be one or more suggestions for improving sleep quality and/or health of the user. The tip can also be suggestions for improving the user's sleep score, tiredness level, alertness level, etc. The tip can also be any other types of suggestions that can be generated based on different types of data associated with the user. In some implementations, a different quantity of tips can be generated per day or some other period of time. The process 600 is merely intended to be an example use case of the data pipeline 100 implementation.

The process 600 can be performed by a combination of components in the data pipeline 100 shown and described in FIG. 1. One or more other services, microservices, and/or computing systems can be used to perform the process 600.

Referring to the process 600, the data pipeline 100 can include a frontend 604 and a backend 606. The frontend 604 can be a frontend API gateway, which can perform aggregation of data from multiple microservices in the backend 606 (e.g., the metrics aggregation microservice 108). The frontend 604 can also be the gateway for applications or software at user devices to call any of the microservices and APIs described in reference to the data pipeline 100.

The backend 606 can handle the microservices of the data pipeline 100. The backend 606 can be multiple layers thick and can also handle different types of user data and historic data, including but not limited to user data, cohort data, health data, etc.

As shown in the process 600, an actor 602 can use their user device to transmit a request to the frontend 604 to generate a tip about a user's data. The request can include the user data. The actor 602 can be the same as the user. The actor 602 may also be different than the user.

The frontend 604 can transmit the request to the backend 606, which can validate/verify the user data (e.g., determine whether the right user is associated with the request, whether the user has enough sleep session data to generate an insight, whether a generic tip should be generated because not enough sleep data is known/collected for the user, etc.)

before engaging the microservices of the data pipeline 100 in generating the tip. As described herein, the frontend 604 can include aggregation microservices that can aggregate the user data and historic data. The aggregated data can be transmitted to the backend 606 for validation. If the user data cannot be validated, then an error message can be transmitted from the backend 606 to the frontend 604, then transmitted as a validation error back to the user device of the actor 602. If validation failed, system messages can be automatically generating for troubleshooting the failure. Sometimes, generic tips can also be generated instead of personalized tips if validation failed.

If, on the other hand, the data can be validated, then the backend 606 can make a Rest API call to the data pipeline 100, requesting the microservices of the data pipeline 100 (e.g., the rule engines 104A-N) to generate the tip based on the data. As described herein, microservices of the data pipeline 100 can generate the tip and persist data. The tip may also be added to the message queue 204 and/or saved in a data store, such as data lake 120A.

The tip can be returned from the data pipeline 100 to the backend 606, then transmitted via the frontend 604 to the user device of the actor 602, or the user device of another relevant user (e.g., the user associated with the data and the generated tip). In some implementations, the tip can be retrieved from the data lake 120A at another time and then returned through the backend 606 and the frontend 604 to the user device of the relevant user.

Figure 7:
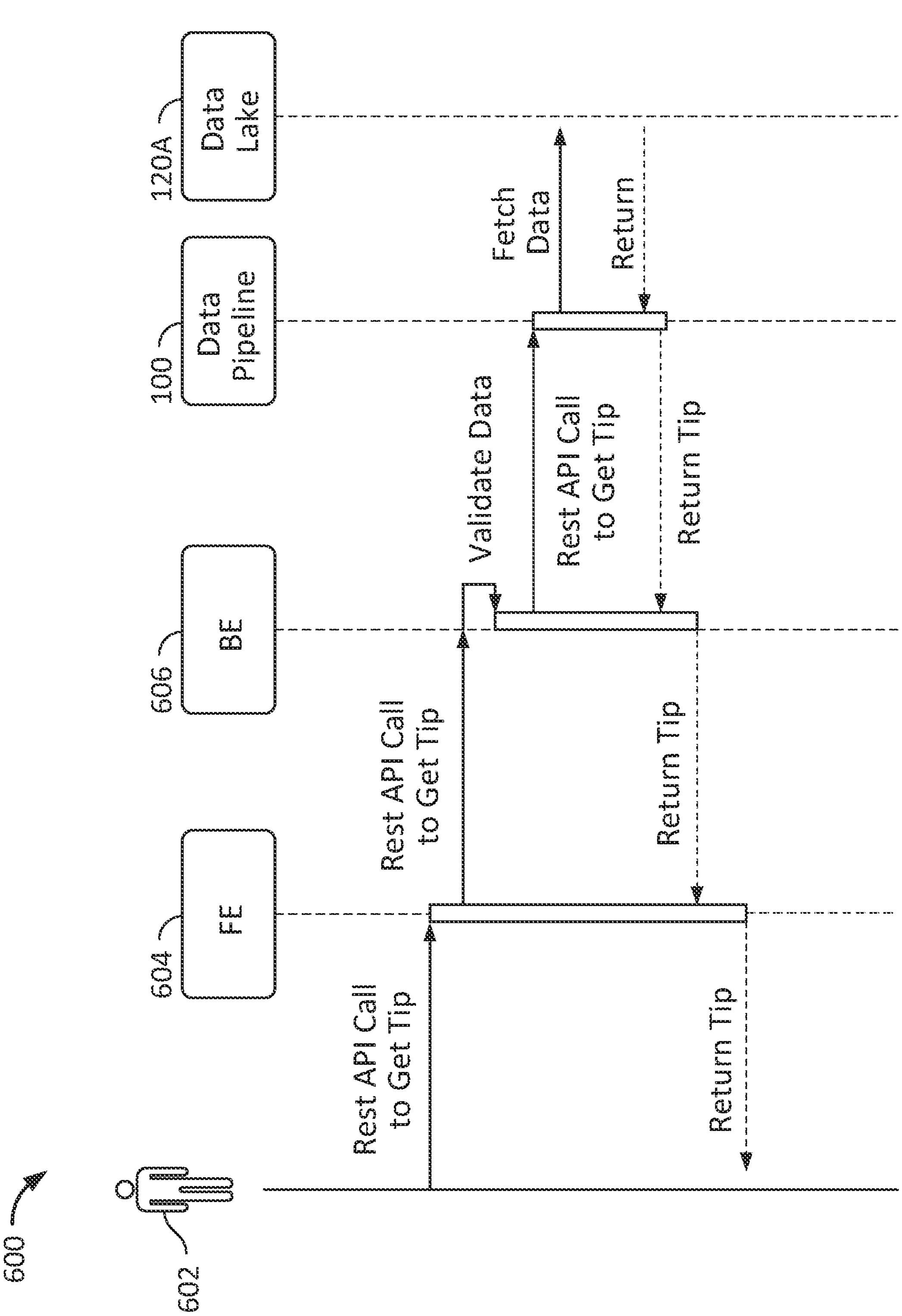
FIG. 7 is a swimlane diagram of a process for retrieving the tip that is generated from the process of FIG. 6.

FIG. 7 is a swimlane diagram of a process 700 for retrieving a tip that is generated (e.g., such as a tip generated using the process of FIG. 6). The tip can be generated in real-time. In some implementations, user input can be received at the frontend 604, such as a current or past alertness level of a user. The user input can then be used to generate the tip. In some implementations, the tip can be retrieved at any time after the tip has been generated using the process 600 in FIG. 6. As shown in the process 700, the actor 602 can use their user device to request to get the tip, as mentioned above. The request can be received at the frontend 604 and transmitted to the backend 606. The backend 606 can validate the data, as described above, and then make a Rest API call to the data pipeline 100 to get the tip that was already generated. One or more microservices of the data pipeline 100 can fetch (e.g., retrieve) the tip from the data lake 120A. The tip can be returned to the user device of the actor 602 through the frontend 604.

Figure 8:
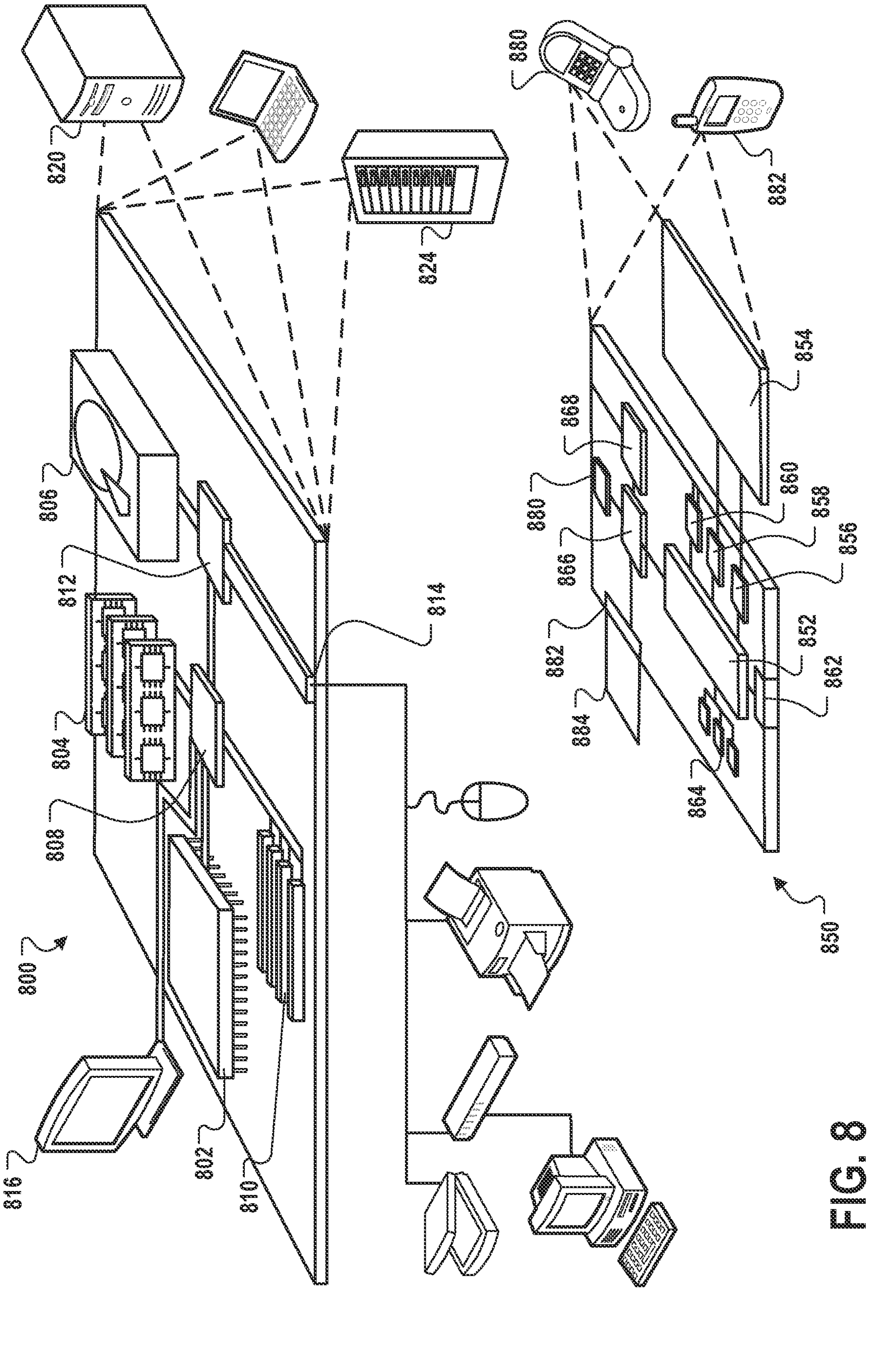
FIG. 8 is a schematic diagram that shows an example of a computing device and a mobile computing device.

FIG. 8 shows an example of a computing device 800 and an example of a mobile computing device that can be used to implement the techniques described here. The computing device 800 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 800 includes a processor 802, a memory 804, a storage device 806, a high-speed interface 808 connecting to the memory 804 and multiple high-speed expansion ports 810, and a low-speed interface 812 connecting to a low-speed expansion port 814 and the storage device 806. Each of the processor 802, the memory 804, the storage device 806, the high-speed interface 808, the high-speed expansion ports 810, and the low-speed interface 812, are interconnected using various busses, and can be mounted on a common motherboard or in other manners as appropriate. The processor 802 can process instructions for execution within the computing device 800, including instructions stored in the memory 804 or on the storage device 806 to display graphical information for a GUI on an external input/output device, such as a display 816 coupled to the high-speed interface 808. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 804 stores information within the computing device 800. In some implementations, the memory 804 is a volatile memory unit or units. In some implementations, the memory 804 is a non-volatile memory unit or units. The memory 804 can also be another form of computer-readable medium, such as a magnetic or optical disk.

The storage device 806 is capable of providing mass storage for the computing device 800. In some implementations, the storage device 806 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 804, the storage device 806, or memory on the processor 802.

The high-speed interface 808 manages bandwidth-intensive operations for the computing device 800, while the low-speed interface 812 manages lower bandwidth-intensive operations. Such allocation of functions is exemplary only. In some implementations, the high-speed interface 808 is coupled to the memory 804, the display 816 (e.g., through a graphics processor or accelerator), and to the high-speed expansion ports 810, which can accept various expansion cards (not shown). In the implementation, the low-speed interface 812 is coupled to the storage device 806 and the low-speed expansion port 814. The low-speed expansion port 814, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 800 can be implemented in a number of different forms, as shown in the figure. For example, it can be implemented as a standard server 820, or multiple times in a group of such servers. In addition, it can be implemented in a personal computer such as a laptop computer 822. It can also be implemented as part of a rack server system 824. Alternatively, components from the computing device 800 can be combined with other components in a mobile device (not shown), such as a mobile computing device 850. Each of such devices can contain one or more of the computing device 800 and the mobile computing device 850, and an entire system can be made up of multiple computing devices communicating with each other.

The mobile computing device 850 includes a processor 852, a memory 864, an input/output device such as a display 854, a communication interface 866, and a transceiver 868, among other components. The mobile computing device 850 can also be provided with a storage device, such as a micro-drive or other device, to provide additional storage. Each of the processor 852, the memory 864, the display 854, the communication interface 866, and the transceiver 868, are interconnected using various buses, and several of the components can be mounted on a common motherboard or in other manners as appropriate.

The processor 852 can execute instructions within the mobile computing device 850, including instructions stored in the memory 864. The processor 852 can be implemented as a chipset of chips that include separate and multiple analog and digital processors. The processor 852 can provide, for example, for coordination of the other components of the mobile computing device 850, such as control of user interfaces, applications run by the mobile computing device 850, and wireless communication by the mobile computing device 850.

The processor 852 can communicate with a user through a control interface 858 and a display interface 856 coupled to the display 854. The display 854 can be, for example, a TFT (Thin-Film-Transistor Liquid Crystal Display) display or an OLED (Organic Light Emitting Diode) display, or other appropriate display technology. The display interface 856 can comprise appropriate circuitry for driving the display 854 to present graphical and other information to a user. The control interface 858 can receive commands from a user and convert them for submission to the processor 852. In addition, an external interface 862 can provide communication with the processor 852, so as to enable near area communication of the mobile computing device 850 with other devices. The external interface 862 can provide, for example, for wired communication in some implementations, or for wireless communication in other implementations, and multiple interfaces can also be used.

The memory 864 stores information within the mobile computing device 850. The memory 864 can be implemented as one or more of a computer-readable medium or media, a volatile memory unit or units, or a non-volatile memory unit or units. An expansion memory 874 can also be provided and connected to the mobile computing device 850 through an expansion interface 872, which can include, for example, a SIMM (Single In Line Memory Module) card interface. The expansion memory 874 can provide extra storage space for the mobile computing device 850, or can also store applications or other information for the mobile computing device 850. Specifically, the expansion memory 874 can include instructions to carry out or supplement the processes described above, and can include secure information also. Thus, for example, the expansion memory 874 can be provide as a security module for the mobile computing device 850, and can be programmed with instructions that permit secure use of the mobile computing device 850. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 864, the expansion memory 874, or memory on the processor 852. In some implementations, the computer program product can be received in a propagated signal, for example, over the transceiver 868 or the external interface 862.

The mobile computing device 850 can communicate wirelessly through the communication interface 866, which can include digital signal processing circuitry where necessary. The communication interface 866 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 868 using a radio-frequency. In addition, short-range communication can occur, such as using a Bluetooth, WiFi, or other such transceiver (not shown). In addition, a GPS (Global Positioning System) receiver module 870 can provide additional navigation- and location-related wireless data to the mobile computing device 850, which can be used as appropriate by applications running on the mobile computing device 850.

The mobile computing device 850 can also communicate audibly using an audio codec 860, which can receive spoken information from a user and convert it to usable digital information. The audio codec 860 can likewise generate audible sound for a user, such as through a speaker, e.g., in a handset of the mobile computing device 850. Such sound can include sound from voice telephone calls, can include recorded sound (e.g., voice messages, music files, etc.) and can also include sound generated by applications operating on the mobile computing device 850.

The mobile computing device 850 can be implemented in a number of different forms, as shown in the figure. For example, it can be implemented as a cellular telephone 880. It can also be implemented as part of a smart-phone 882, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

What is claimed is:

1. A system for managing data for determining personalized data for many users, wherein the personalized data indicates trends based on aggregated user data and aggregated historic data, wherein the personalized data comprises a score selected from the group consisting of a sleep score, a quality of sleep score, and a user health score, the system comprising one or more processors:

a startup manager microservice configured to:

receive user input to begin batch processing of user data;

receive the user data in real-time; and run data definition language (DDL) and data manipulation language (DML) scripts at a data store to prepare the data store to be used by one or more other microservices;

one or more rule engines that generate personalized data based at least in part on the received user data, wherein the one or more rule engines are configured to:

import, by a rules importer microservice of the rule engine, one or more rules to the data store, wherein the one or more imported rules include message templates storing data in a machine-readable format from which readable messages can be generated for output generated by applying the one or more imported rules to the received user data;

parse, by a rules partitioning microservice of the rule engine, the one or more rules to identify the message templates corresponding to each of the one or more rules; and store, by the rules partitioning microservice of the rule engine, the message templates and the parsed rules in persistent metadata;

a metrics aggregation microservice that is configured to receive the user data from a current sleep session from the startup manager microservice and aggregate the user data in real-time;

a historic import microservice configured to:

retrieve, from a data repository, historic data about a user's previous sleep sessions; and aggregate the historic data;

a message repository microservice configured to store, in the data store, messages generated by the one or more rule engines using the corresponding message templates; and a synchronization microservice configured to provide communication between the system and one or more user devices, wherein the messages generated by the one or more rule engines and stored by the message repository microservice are retrieved, by the synchronization microservice, and transmitted to the one or more user devices for presentation in a graphical user interface (GUI) display of the one or more user devices, wherein each of the one or more rule engines is further configured to:

receive, from the metrics aggregation microservice, the aggregated user data;

receive, from the historic import microservice, the aggregated historic data;

determine, based on the aggregated user data and the aggregated historic data, whether one or more of the parsed rules are satisfied;

generate, based on determining whether one or more of the parsed rules are satisfied, personalized data for the user associated with the aggregated user data;

generate, based on determining whether one or more of the parsed rules are satisfied, messages to be presented at the one or more user devices using one or more of the corresponding message templates, wherein the messages include the generated personalized data; and transmit the generated messages to the message repository microservice for storage.

2. The system of claim 1, wherein each of the one or more rule engines includes a rule file that indicates (i) a type of personalized data that is determined by the rule engine, (ii)

criteria for determining the type of personalized data, and (iii) criteria for a type of output to generate using a corresponding message template.

3. The system of claim 1, wherein the message templates are used, by the one or more rule engines, to generate the messages in a readable format for users of the one or more user devices.

4. The system of claim 1, wherein at least one of the rule engines is configured to generate personalized data for the user that indicates monthly or weekly trends based on the aggregated user data and the aggregated historic data.

5. The system of claim 1, wherein at least one of the rule engines is a rule-based engine that is configured to generate monthly health quality scores for the user based on the aggregated user data and the aggregated historic data.

6. The system of claim 1, wherein at least one of the rule engines is a rule-based engine that is configured to generate monthly sleep quality scores for the user based on the aggregated user data and the aggregated historic data.

7. The system of claim 1, wherein at least one of the rule engines is artificial intelligence (AI)-based and is configured to:

generate messages about the personalized data for the user; and prioritize, using models, trained with machine learning, and based on the personalized data, sharing of the messages with the one or more user devices.

8. The system of claim 1, wherein at least one of the rule engines is a hybrid of a rule-based and AI-based engine that is configured to generate personalized data about the user based on the aggregated user data and the aggregated historic data.

9. The system of claim 1, wherein the one or more rule engines are executed in parallel.

10. The system of claim 1, wherein each of the one or more rule engines is further configured to randomize delivery of the messages to the one or more user devices.

11. The system of claim 1, wherein the user data includes at least one of sleep data, health data, and biometrics data.

12. The system of claim 1, wherein the user data is detected by components of a bed system and transmitted to the startup manager microservice by a controller of the bed system.

13. The system of claim 1, wherein the metrics aggregation microservice is further configured to aggregate the user data on at least one of a weekend, weekday, daily, weekly, monthly, and yearly basis.

14. The system of claim 1, wherein the message repository microservice is configured to:

store the generated messages in the data store for a predetermined period of time; and archive the generated messages once the predetermined period of time ends.

15. The system of claim 14, wherein the predetermined period of time is 3 months from at least one of collection of the user data and determination of the personalized data.

16. The system of claim 1, wherein one or more of the microservices of the system communicate by a simple queue service (SQS) message queue.

17. The system of claim 1, wherein the personalized data includes one or more suggestions for the user to improve at least one of their sleep and health.

18. A system for managing data for determining personalized data for many users, wherein the personalized data indicates trends based on aggregated user data and aggregated historic data, wherein the personalized data comprises a score selected from the group consisting of a sleep score, a quality of sleep score, and a user health score, the system comprising one or more processors:

a startup manager microservice configured to:

receive user input to begin batch processing of user data;

receive the user data in near real-time; and run data definition language (DDL) and data manipulation language (DML) scripts at a data store to prepare the data store to be used by one or more other microservices;

one or more rule engines that generate personalized data based at least in part on the received user data, wherein the one or more rule engines are configured to:

import, by a rules importer microservice of the rule engine, one or more rules to the data store, wherein the one or more imported rules include message templates for output generated by applying the one or more imported rules to the received user data;

parse, by a rules partitioning microservice of the rule engine, the one or more rules to identify the message templates corresponding to each of the one or more rules; and store, by the rules partitioning microservice of the rule engine, the message templates and the parsed rules in persistent metadata;

a metrics aggregation microservice that is configured to receive the user data from the startup manager microservice and aggregate the user data in near real-time;

a historic import microservice configured to:

retrieve, from a data repository, historic data about a user that is associated with the user data; and aggregate the historic data;

a message repository microservice configured to store, in the data store, messages generated by the one or more rule engines using the corresponding message templates; and a synchronization microservice configured to provide communication between the system and one or more user devices, wherein the messages generated by the one or more rule engines and stored by the message repository microservice are retrieved, by the synchronization microservice, and transmitted to the one or more user devices for presentation in a graphical user interface (GUI) display of the one or more user devices, wherein each of the one or more rule engines is further configured to:

receive, from the metrics aggregation microservice, the aggregated user data;

receive, from the historic import microservice, the aggregated historic data;

determine, based on the aggregated user data and the aggregated historic data, whether one or more of the parsed rules are satisfied;

generate, based on determining whether one or more of the parsed rules are satisfied, personalized data for the user associated with the aggregated user data;

generate, based on determining whether one or more of the parsed rules are satisfied, messages to be presented at the one or more user devices using one or more of the corresponding message templates, wherein the messages include the generated personalized data; and transmit the generated messages to the message repository microservice for storage;

wherein each of the one or more rule engines includes a rule file that indicates (i) a type of personalized data that is determined by the rule engine, (ii) criteria for determining the type of personalized data, and (iii) criteria for a type of output to generate using a corresponding message template;

wherein (ii) further includes a time period associated with the personalized data, wherein the time period is at least one of a weekend, a day, a group of days, a week, a month, or a year.

19. A system for managing data for determining personalized data for many users, wherein the personalized data indicates trends based on aggregated user data and aggregated historic data, wherein the personalized data comprises a score selected from the group consisting of a sleep score, a quality of sleep score, and a user health score, the system comprising one or more processors:

a startup manager microservice configured to:

receive user input to begin batch processing of user data;

receive the user data in near real-time; and run data definition language (DDL) and data manipulation language (DML) scripts at a data store to prepare the data store to be used by one or more other microservices;

one or more rule engines that generate personalized data based at least in part on the received user data, wherein the one or more rule engines are configured to:

import, by a rules importer microservice of the rule engine, one or more rules to the data store, wherein the one or more imported rules include message templates for output generated by applying the one or more imported rules to the received user data;

parse, by a rules partitioning microservice of the rule engine, the one or more rules to identify the message templates corresponding to each of the one or more rules; and store, by the rules partitioning microservice of the rule engine, the message templates and the parsed rules in persistent metadata;

a metrics aggregation microservice that is configured to receive the user data from the startup manager microservice and aggregate the user data in near real-time;

a historic import microservice configured to:

retrieve, from a data repository, historic data about a user that is associated with the user data; and aggregate the historic data;

a message repository microservice configured to store, in the data store, messages generated by the one or more rule engines using the corresponding message templates; and a synchronization microservice configured to provide communication between the system and one or more user devices, wherein the messages generated by the one or more rule engines and stored by the message repository microservice are retrieved, by the synchronization microservice, and transmitted to the one or more user devices for presentation in a graphical user interface (GUI) display of the one or more user devices, wherein each of the one or more rule engines is further configured to:

receive, from the metrics aggregation microservice, the aggregated user data;

receive, from the historic import microservice, the aggregated historic data;

determine, based on the aggregated user data and the aggregated historic data, whether one or more of the parsed rules are satisfied;

generate, based on determining whether one or more of the parsed rules are satisfied, personalized data for the user associated with the aggregated user data;

generate, based on determining whether one or more of the parsed rules are satisfied, messages to be presented at the one or more user devices using one or more of the corresponding message templates, wherein the messages include the generated personalized data; and transmit the generated messages to the message repository microservice for storage;

wherein the user data is received, by the startup manager microservice, in real-time during sleep sessions of the user.

* * * * *